United States Patent
Mao et al.

(10) Patent No.: US 9,193,746 B2
(45) Date of Patent: Nov. 24, 2015

(54) LUMINESCENT METAL COMPLEXES AND ASSOCIATED TECHNOLOGY

(75) Inventors: Fei Mao, Fremont, CA (US); Wai-Yee Leung, San Ramon, CA (US); Ching-Ying Cheung, San Ramon, CA (US); Jie Yang, Albany, CA (US)

(73) Assignee: BIOTIUM, INC., Hayward, CA (US)

( * ) Notice: Subject to any disclaimer, the term of this patent is extended or adjusted under 35 U.S.C. 154(b) by 790 days.

(21) Appl. No.: 11/952,867

(22) Filed: Dec. 7, 2007

(65) Prior Publication Data

US 2008/0145526 A1 Jun. 19, 2008

Related U.S. Application Data

(60) Provisional application No. 60/869,075, filed on Dec. 7, 2006.

(51) Int. Cl.
  *G01N 21/64* (2006.01)
  *C07F 15/00* (2006.01)
  *C09B 57/10* (2006.01)
  *G01N 33/68* (2006.01)

(52) U.S. Cl.
  CPC .............. *C07F 15/0053* (2013.01); *C09B 57/10* (2013.01); *G01N 33/6839* (2013.01); *G01N 2458/40* (2013.01)

(58) Field of Classification Search
  CPC ................ C07F 15/0053; C09B 57/10; G01N 2458/40; G01N 33/6839
  See application file for complete search history.

(56) References Cited

U.S. PATENT DOCUMENTS

| | | | |
|---|---|---|---|
| 5,278,043 A * | 1/1994 | Bannwarth et al. | 536/23.1 |
| 5,403,928 A | 4/1995 | Arrhenuis | |
| 5,453,356 A * | 9/1995 | Bard et al. | 435/6 |
| 6,316,267 B1 | 11/2001 | Bhalgat et al. | |
| 6,329,205 B1 * | 12/2001 | Diwu et al. | 436/86 |
| 2002/0135780 A1* | 9/2002 | Budach et al. | 356/521 |
| 2008/0006322 A1* | 1/2008 | Wang et al. | 136/252 |

FOREIGN PATENT DOCUMENTS

WO   WO 97/20213 A1   6/1997

OTHER PUBLICATIONS

Alford, et al. Luminescent metal complexes. Part 5. Luminescence properties of ring-substituted 1.10-phenanthroline tris-complexes of ruthenium(II). J. Chem. Soc. Perkin. Trans. II. 1985; 705-709.

(Continued)

*Primary Examiner* — Dirk Bass
(74) *Attorney, Agent, or Firm* — Wilson Sonsini Goodrich & Rosati

(57) ABSTRACT

Luminescent metal complexes, methods of producing and/or designing same, methods of using same, and associated technology, are disclosed herein. A luminescent metal complex may be useful for a variety of applications, such as staining, detection, and/or identification, for example, of substances, such as poly(amino acids), for example. Further by way of example, a luminescent metal complex may be useful for staining, detecting, and/or identifying poly(amino acids) that are associated with any of various environments, such as a gel or a gel matrix, such as any associated with SDS-PAGE, for example, a surface environment, such as any associated with western blot, for example, and/or the like. Compositions, solutions, and kits comprising a luminescent metal complex are also disclosed herein.

15 Claims, 5 Drawing Sheets

Excitation and Emission Spectra of Complex No. 4

(56) References Cited

OTHER PUBLICATIONS

Collins, et al. Ruthenium(II) alpha-Diimine Complexes with One, Two, and Three 4,4'-Bis(hydroxymethyl)-2,2'-bipyridine and 4,4'-Bis(chloromethyl)-2,2'-bipyridine Ligands: Useful Starting Materials for Further Derivatization. Inorg. Chem. 1999; 38: 2020-2024.

Garcia-Fresnadillo, et al. Photosensitized Generation of Singlet Oxygen from (Substituted Bipyridine)ruthennim(II) Complexes Helv. Chim Acta. 2001; 84; 2708-2730.

Guo, et al. A long-lived, highly luminescent Re(I) metal-ligand complex as a biomolecular probe. Anal Biochem. 1997; 254;179-186.

Lamanda, et al. Improved Ruthenium II tris (bathophenantroline disulfonate) staining and destaining protocol for a better signal-to-background ratio and improved baseline resolution. Proteomics. 2004; 4: 599-608.

LI, et al. Long-lifetime lipid rhenium metal-ligand complex for probing membrane dynamics on the microsecond timescale. Chem. Phys. Lipids. 1999; 99:1-93.

MacIntosh, et al. A fluorescent natural product for ultra sensitive detection of proteins in one-dimensional and two-dimensional gel electrophoresis. Proteomics. 2003; 3: 2273-2288.

Material Safety Data Sheet. GFS Chemicals, Inc, Paper print-out from www.gfschemical.com/chemicals/gfschem-1597.asp. Accessed on Nov. 13, 2006.

Nishihara, et al. Quantitative evaluation of proteins in one- and two-dimensional polyacrylamide gels using a fluorescent stain. Electrophoresis. 2002; 23: 2203-2215.

Rabilloud, et al. A comparison between Sypro Ruby and ruthenium II tris (bathophenanthroline disulfonate) as fluorescent stains for protein detection in gels. Proteomics. 2001; 1:699-704.

Smithback, et al. Preparative routes to luminescent mixed-ligand rhenium(I) dicarbonyl complexes. Inorg. Chem. 2006:45: 2163-2174.

Steinberg, et al. Ultrasensitive fluorescence protein detection in isoelectric focusing gels using a ruthenium metal chelate stain. Electrophoresis. 2000; 21: 486-496.

Steinberg, et al. SYPRO orange and SYPRO red protein gel stains: one-step fluorescent staining of denaturing gels for detection of nanogram levels of protein. Anal Biochem. 1996; 239: 223-237.

Wang, et al. Covalent Attachment of RuII Phenanthroline Complexes to polythionylphosphazenes: The Development and Evaluation of Single-Component Polymeric Oxygen Sensors Adv. Funct. Mater. 2002; 12:415-419.

* cited by examiner

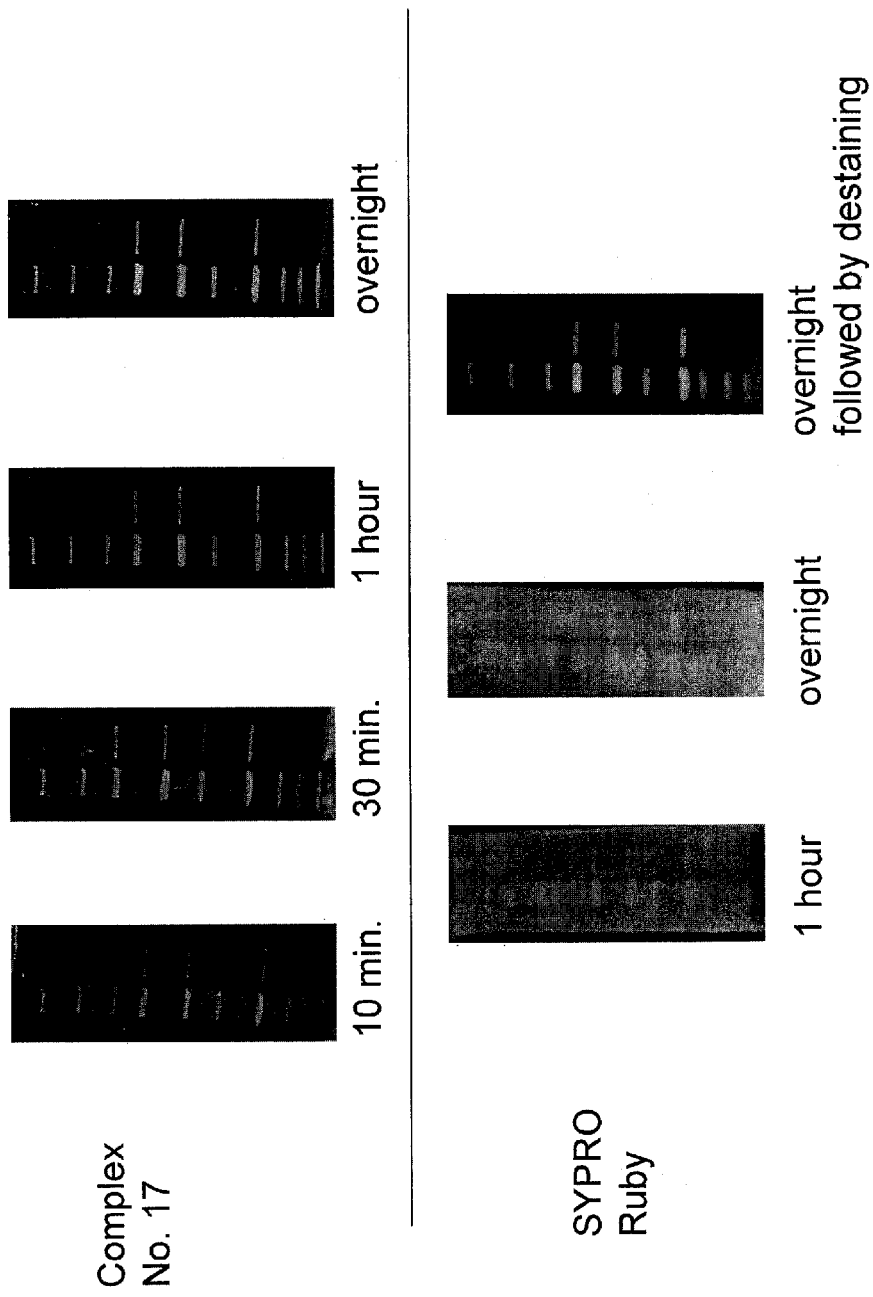
FIG. 1 Detection of Proteins in SDS-PAGE Gel Using Complex No. 17 or SYPRO Ruby

FIG. 2 Detection of Proteins in SDS-PAGE Gel Using Complex No. 4
4 hours
without destaining
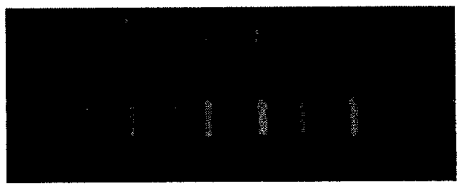
overnight
without destaining

FIG. 3 Detection of Proteins in SDS-PAGE Gel Using Complex No. 2
Overnight without destaining

FIG. 4 Detection of Proteins in SDS-PAGE Gel Using Complex [Ru(bpy)$_3$]Cl$_2$, [Ru(1,10-phenanthroline)$_3$]Cl$_2$, or Complex No. 22

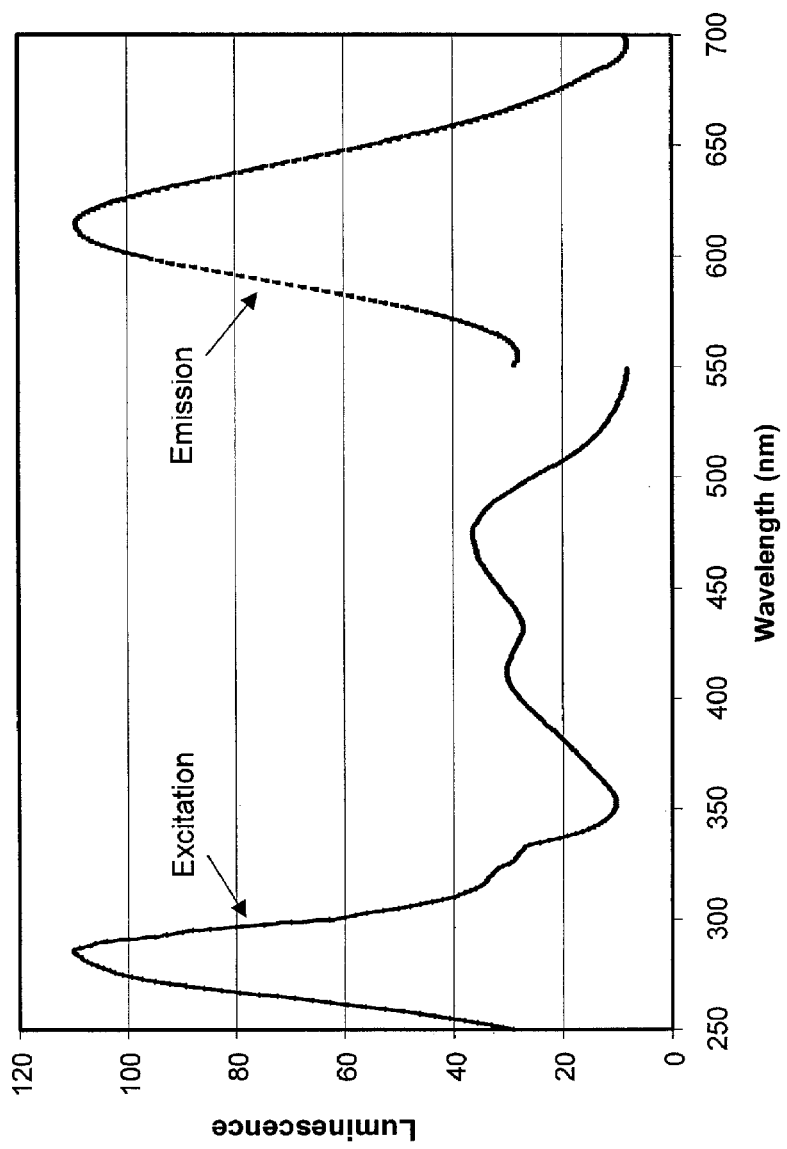
FIG. 5 Excitation and Emission Spectra of Complex No. 4

LUMINESCENT METAL COMPLEXES AND ASSOCIATED TECHNOLOGY

CROSS-REFERENCE

This application claims the benefit of U.S. Provisional Application No. 60/869,075, filed Dec. 7, 2006, which application is incorporated herein by reference in its entirety.

BACKGROUND OF THE INVENTION

Purification and analysis of poly(amino acids), such as proteins, for example, may be employed in various biological studies. Generally, in protein purification and analysis, a mixture of proteins may be separated into distinct protein molecules and the separated protein molecules may be quantified. Using such processes, researchers may detect and/or identify various proteins and may study how proteins are expressed and/or modified in a biological system. The expression level and/or modification of various proteins may be correlated with biological phenotypes and/or disease states. Protein purification and analysis may thus have useful application in the diagnosis and/or prognosis of disease.

Sodium dodecyl sulfate polyacrylamide gel electrophoresis (SDS-PAGE) is a method that may be used in the separation and quantification of proteins. In such a method, a protein sample may be placed in denaturing and reducing conditions and heated such that the proteins unfold. The unfolded proteins may be coated with sodium dodecyl sulfate (SDS) detergent molecules, such that they take on an overall negative or anionic charge that is proportional to the size of the proteins. The SDS-coated proteins may be loaded onto a gel matrix and placed in an electric field, such that the negatively or anionically charged proteins migrate towards a positively or cationically charged anode electrode and separate into bands according to their molecular sizes. Since most proteins are colorless, the separated proteins may be stained using a protein stain that imparts color to the proteins, such as an absorption color that is light-absorptive in the presence of light, a fluorescence color that is fluorescent in the presence of light, or a luminescence color that is luminescent in the presence of light, for example. Stained proteins may be visualized, sensed, or detected in the presence of light.

Various protein stains may be used to stain proteins. For example, there are various protein stains that may be used to stain proteins that may be associated with, such as being present on or in, for example, gels or other media. Examples of protein gel stains include a stain comprising a silver compound, which may be referred to as a silver stain, Coomassie Blue (CB), which is an absorption color-based stain, and SYPRO Orange, SYPRO Red, and Deep Purple stains, which are fluorescence color-based stains. Each of these stains is associated with various disadvantages, such as those mentioned in U.S. Pat. No. 6,316,267, for example.

The foregoing may also apply to poly(amino acids), of which proteins and peptides, for example, are subsets. Development of applications, such as staining, detection, and/or identification, for example, of substances, such as poly(amino acids), peptides, and/or proteins, for example, useful compositions therefor, the making thereof, the use thereof, and/or associated technology is generally desirable.

SUMMARY OF THE INVENTION

Luminescent metal complexes, methods of producing and/or designing same, methods of using same, and associated technology, are disclosed herein. Such a luminescent metal complex (which hereinafter may be referred to as a luminescent metal complex, a luminescent complex, a metal complex, or a complex) may be useful for a variety of applications. By way of example, a luminescent metal complex may be useful in the staining, detection, and/or identification, for example, of substances, such as poly(amino acids), proteins, and/or peptides, for example. Further by way of example, a luminescent metal complex may be useful for staining, detecting, and/or identifying, for example, poly(amino acids), proteins, and/or peptides, for example, associated with, such as on or in, for example, any of various environments, such as a gel, a gel matrix, and/or a surface environment, for example. Examples of such environments include a medium associated with SDS-PAGE, such as a gel or a gel matrix, for example, a surface associated with western blot, such as solid surface or a membrane surface, for example, and/or the like.

In terms of staining, detection, and/or identification of poly(amino acids) associated with a sample, for example, the sample may or may not include poly(amino acids). For example, a purpose of such staining, detection, and/or identification may be to determine whether poly(amino acids) are present or absent in the sample. As such, staining applications may include employing a solution comprising a luminescent metal complex in connection with a sample to stain poly (amino acids) should they be present in the sample or to fail to stain poly(amino acids) should they be absent from the sample. As such, detection and/or identification of poly (amino acids) may include employing a solution comprising a luminescent metal complex in connection with a sample to detect and/or to identify poly(amino acids) should they be present in the sample or to fail to detect and/or to identify poly(amino acids) should they be absent from the sample. Detection and/or identification of poly(amino acids) in a sample, may comprise employing a solution comprising a luminescent metal complex in connection with a sample to detect light emission, such as luminescence or fluorescence, for example, or lack of light emission, such as luminescence or fluorescence, for example.

A luminescent metal complex may comprise at least one counter ion. A luminescent complex exclusive of any such counter ion(s) may be associated with at least one positive or cationic net charge. For example, if the complex were dissolved in solution, the portion of the complex exclusive of any counter ion(s) may be associated with at least one positive or cationic net charge or said to be positively or cationically net charged. In this context, "net charge" or "net charged" indicates that while this portion of the complex may contain positive charge(s), or both positive charge(s) and negative charge(s), when these charges are tallied (added and/or subtracted, according to the number of positive charge(s) and/or the number of negative charge(s), respectively), the resulting tally, or net, is at least one positive charge. With this in mind, such a portion of a luminescent metal complex may be said to be positively or cationically net charged, although when the overall complex including any counter ion(s) is considered, the overall complex may be neutral or balanced in terms of charge. In some cases, a luminescent metal complex exclusive of any counter ion(s) may be associated with a neutral net charge or a negative or an anionic net charge, and said to be neutrally or negatively or anionically net charged, respectively, although when the overall complex including any counter ion(s) is considered, the overall complex may be neutral or balanced in terms of charge.

A luminescent metal complex may be relatively lipophilic. For example, a luminescent metal complex may comprise a transition metal and at least one ligand sufficient to render the luminescent metal complex relatively lipophilic. Lipophilicity may be determined by screening, as further described herein. A luminescent metal complex may be sufficient to interact or capable of interacting with poly(amino acids) in a useful manner, such as to stain the poly(amino acids). Examples of such interaction include hydrophobic interaction and electrostatic interaction. By way of example, such interaction may be hydrophobic and optionally electrostatic.

A method of using a luminescent metal complex may comprise exposing a sample to at least one luminescent metal complex, such as via a solution comprising at least one luminescent metal complex. Such a solution, or such a complex thereof, may be sufficient to interact or capable of interacting with poly(amino acids) of the sample, if any, such as in any suitable manner described herein, for example; to stain poly(amino acids) of the sample, if any, such as in any suitable manner described herein, for example; and/or to detect and/or identify poly(amino acids) of the sample, if any, such as in any suitable manner described herein, for example.

A composition may comprise a luminescent metal complex having a structural formula such as that (namely, Formula 1) set forth below.

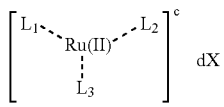

Formula 1

In the complex of Formula 1, $L_1$, $L_2$, and $L_3$ are unsubstituted or substituted with a total of no more than two negatively charged sulfonate groups such that net charge c is not negative, i.e. it can be neutral (0), or charged positively (e.g. 1+ or 2+). In some embodiments, the total number of negatively charged sulfonate groups in the complex of Formula 1 is 1. In some embodiments, the total number of negatively charged sulfonate groups in the complex of Formula 1 is 0. In some embodiments, $L_1$ may be a ligand selected from a 2,2'-bipyridine, a neutrally-substituted 2,2'-bipyridine comprising less than 23 carbon atoms, a 1,10-phenanthroline, and a neutrally substituted 1,10-phenanthroline comprising less than 25 carbon atoms. In some embodiments, $L_2$ may be a ligand selected from a 2,2'-bipyridine, a neutrally-substituted 2,2'-bipyridine comprising less than 23 carbon atoms, a 1,10-phenanthroline, and a neutrally substituted 1,10-phenanthroline comprising less than 25 carbon atoms. $L_1$ and $L_2$ may be the same or may be different. In some embodiments, $L_1$ is a ligand selected from 2,2'-bipyridine, 4,4'-dimethyl-2,2'-bipyridine, 3,4,3',4'-tetramethyl-2,2'-bipyridine, 4,4'-diphenyl-2,2'-bipyridine, 1,10-phenanthroline, 4-methyl-1,10-phenanthroline, 5-methyl-1,10-phenanthroline, 4,7-dimethyl-1,10-phenanthroline, 5,6-dimethyl-1,10-phenanthroline, 3,4,7,8-tetramethyl-1,10-phenanthroline, 5-phenyl-1,10-phenanthroline, bathophenanthroline, and 5-chloro-1,10-phenanthroline, any of which is unsubstituted or substituted with one sulfonate group, providing that the condition of a total of no more than two negatively charged sulfonate groups in the complex of Formula I is met. In some embodiments, $L_2$ may be a ligand selected from 2,2'-bipyridine, 4,4'-dimethyl-2,2'-bipyridine, 3,4,3',4'-tetramethyl-2,2'-bipyridine, 4,4'-diphenyl-2,2'-bipyridine, 1,10-phenanthroline, 4-methyl-1,10-phenanthroline, 5-methyl-1,10-phenanthroline, 4,7-dimethyl-1,10-phenanthroline, 5,6-dimethyl-1,10-phenanthroline, 3,4,7,8-tetramethyl-1,10-phenanthroline, 5-phenyl-1,10-phenanthroline, bathophenanthroline, and 5-chloro-1,10-phenanthroline, any of which is unsubstituted or substituted with one sulfonate group, providing that the condition of a total of no more than two negatively charged sulfonate groups in the complex of Formula I is met.

In some embodiments, $L_3$ may be a ligand selected from a substituted 2,2'-bipyridine and a substituted 1,10-phenanthroline, providing that the condition of a total of no more than two negatively charged sulfonate groups in the complex of Formula 1 is met.

At least one ligand selected from ligand $L_1$, ligand $L_2$, and ligand $L_3$ may be sufficient to render the complex relatively lipophilic. By way of example, such a ligand or ligands may be relatively lipophilic or may comprise at least one substituent that may be relatively lipophilic, such as in a manner described herein, for example, such that the metal complex is relatively lipophilic. At least one of the ligands selected from ligand $L_1$, ligand $L_2$, and ligand $L_3$ may be sufficient to interact or capable of interacting with poly(amino acids), such as in a manner described herein, may be sufficient to render the luminescent metal complex sufficient to stain or capable of staining poly(amino acids), such as in a manner described herein, may be sufficient to render the luminescent metal complex sufficient to detect and/or identify or capable of detecting and/or identifying poly(amino acids), such as in a manner described herein, and/or the like. Such a luminescent metal complex may comprise a charge, c, of 1+ or 2+; a counter ion or an anion, X; and a number, d, of counter ion(s) or anion(s) X, such as that sufficient to balance or to neutralize the charge, c, for example. In Formula 1, the charge, c, may be recognized as a "net charge" of the complex exclusive of its counter ion(s), dX, in the manner described above.

In some embodiments, $L_3$ of Formula 1 may be a ligand represented by a structural formula, such as that (namely, Formula 2) set for the below.

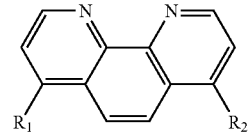

Formula 2

In such a case, $R_1$ may be —H, phenyl, or sulfophenyl; and $R_2$ may be a C6 to C22 alkyl, the alkyl optionally comprising at least one hetero atom selected from halogen, nitrogen, oxygen, and sulfur; a phenyl, substituted with a C1 to C18 alkylaminosulfo substituent, wherein the alkyl thereof is linear or branched and optionally comprises an aryl and/or at least one oxygen atom; or a phenyl, substituted with a C2 to C24 dialkylaminosulfo substituent, wherein the dialkyl thereof is linear or branched, optionally comprises an aryl and/or at least one oxygen atom, and optionally forms a saturated or unsaturated, substituted or unsubstituted, 4- to 7-membered ring.

A solution comprising a luminescent metal complex, such as any described herein, for example, may have any of a variety of useful applications, such as staining, detecting, and/or identifying applications, such as any of those described herein, for example. The luminescent metal complex may comprise at least one counter ion and may be associated with charge neutrality, as mentioned above. The luminescent metal complex may comprise a transition metal and at least one ligand sufficient to render the luminescent metal complex relatively lipophilic. A concentration of the luminescent metal complex in the solution may be from about 0.05

μM to about 5 μM, inclusive, relative to the solution. Such a solution may comprise at least one water-miscible organic solvent, such as methanol and/or ethanol, for example. Such a solution may comprise at least one component selected from an acid, a buffering agent, an inorganic salt, a metal-chelating agent, a detergent, and/or a reducing agent. Such a solution may be aqueous.

A kit comprising a luminescent metal complex, such as any described herein, for example, or a solution, such as any described herein, for example, may have any of a variety of useful applications, such as staining, detecting, and/or identifying applications, such as any of those described herein, for example. Such a kit may comprise information, such as any concerning an application or a use of the complex, the solution, or the kit; at least one agent suitable for such an application or a use, such as a buffer, a protein ladder, agarose, acrylamide, and/or polyacrylamide, for example; and/or the like.

These and various other aspects, features, and embodiments are further described herein. Merely by way of example, a composition, a luminescent metal complex, a solution, a kit, and/or a method described herein may be useful for purposes described herein, such as determining presence or absence of poly(amino acids) in a sample, for example. Any other portion of this application is incorporated by reference in this summary to the extent same may facilitate a summary of subject matter described herein, such as subject matter appearing in any claim or claims that may be associated with this application.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

A description of various aspects, features, embodiments, and examples is provided herein with reference to the accompanying drawings, which are briefly described below. The drawings may illustrate one or more aspect(s), feature(s), embodiment(s), and/or example(s) in whole or in part. The drawings are illustrative and are not necessarily drawn to scale.

FIG. 1 shows photographs of two SDS-PAGE gels, one shown in the top four photographs, and the other shown in the bottom three photographs, as further described in Example 15. For each gel, the left column was loaded with a protein standard and the right column was loaded with the same standard diluted 5 times, prior to electrophoretic separation. Following electrophoretic separation, one gel was stained with Complex No. 17 of Table 1, and the other gel was stained with SYPRO Ruby protein gel stain, for different amounts of time, as indicated. Each of the gels was not destained before being photographed, unless indicated otherwise.

FIG. 2 shows two photographs of an SDS-PAGE gel, as further described in Example 16. The left column of the gel was loaded with a protein standard and the right column of the gel was loaded with the same standard diluted 5 times, prior to electrophoretic separation. Following electrophoretic separation, the gel was stained with Complex No. 4 of Table 1, for different amounts of time, as indicated. The gel was not destained before being photographed.

FIG. 3 shows a photograph of an SDS-PAGE gel, as further described in Example 17. The left column of the gel was loaded with a protein standard and the right column of the gel was loaded with the same standard diluted 5 times, prior to electrophoretic separation. Following electrophoretic separation, the gel was stained with Complex No. 2 of Table 1. The gel was not destained before being photographed.

FIG. 4 shows photographs of three SDS-PAGE gels, as further described in Example 17. For each gel, the left column was loaded with a protein standard and the right column was loaded with the same standard diluted 5 times, prior to electrophoretic separation. Following electrophoretic separation, one of the gels was stained with $[(Ru(bpy)_3]Cl_2$, where bpy is 2,2'-bipyridine, as shown in the left-most photograph, another of the gels was stained with $[Ru(1,10\text{-phenanthroline})_3]Cl_2$, as shown in the middle-most photograph, and the remaining gel was stained with Complex No. 22 of Table 1, as shown in the right-most photograph, for 90 minutes. Each of the gels was not destained before being photographed.

FIG. 5 is a graphical representation of the excitation and emission spectra (normalized luminescence vs. wavelength in nanometers) of Complex No. 4 of Table 1 in water, as further described herein.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

A luminescent metal complex, a composition, a solution, a kit, and/or a method described herein may be useful for purposes described herein, such as determining presence or absence of poly(amino acids) in a sample, for example. A description of various aspects, features, embodiments, and examples, is provided herein.

It will be understood that a word appearing herein in the singular encompasses its plural counterpart, and a word appearing herein in the plural encompasses its singular counterpart, unless implicitly or explicitly understood or stated otherwise. Further, it will be understood that for any given component described herein, any of the possible candidates or alternatives listed for that component, may generally be used individually or in any combination with one another, unless implicitly or explicitly understood or stated otherwise. Additionally, it will be understood that any list of such candidates or alternatives, is merely illustrative, not limiting, unless implicitly or explicitly understood or stated otherwise. Still further, it will be understood that any figure or number or amount presented herein is approximate, and that any numerical range includes the minimum number and the maximum number defining the range, whether the word "inclusive" or the like is employed or not, unless implicitly or explicitly understood or stated otherwise. Yet further, it will be understood that any heading employed is by way of convenience, not by way of limitation. Additionally, it will be understood that any permissive, open, or open-ended language encompasses any relatively permissive to restrictive language, less open to closed language, or less open-ended to closed-ended language, respectively, unless implicitly or explicitly understood or stated otherwise. Merely by way of example, the word "comprising" may encompass "comprising"-, "consisting essentially of"-, and/or "consisting of"-type language.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

Various terms may be generally described, defined, and/or used herein to facilitate understanding. It will be understood that a corresponding general description, definition, and/or use of these various terms applies to corresponding linguistic or grammatical variations or forms of these various terms. It will also be understood that a general description, definition, and/or use, or a corresponding general description, definition, and/or use, of any term herein may not apply or may not fully apply when the term is used in a non-general or more specific manner. It will also be understood that the terminology used herein, and/or the descriptions and/or definitions thereof, for the description of particular embodiments, is not limiting. It will further be understood that embodiments described herein or applications described herein, are not limiting, as such may vary.

Generally, the term "poly(amino acids)" may refer to polymers comprising natural or unnatural amino acid monomers covalently linked via peptide bonds. Poly(amino acids) may refer to proteins, peptides, and/or polypeptides, for example.

Generally, the term "immobilized" may be used in connection with a substance or substances, such as poly(amino acids), for example, that may be associated with a medium, such as a gel, a gel matrix, a surface, or a membrane, for example, such as any of same that may be associated with an electrophoretic process, for example. In general, while such a substance may be mobile during an electrophoretic process, such that it may move relative to the medium under the influence of a force or current, for example, it may be so mobile while still remaining associated with the medium. As such, in general, "immobilized" and associated terminology (such as immobilization, for example) may refer to the ongoing association of a substance with a medium during and optionally following an electrophoretic process. Merely by way of example, an immobilized substance associated with a medium generally remains so associated during and optionally following an electrophoretic process, rather than entering into a solution associated with the electrophoretic process, for example, unless and until it becomes or is made to become disassociated with the medium, such as by intentional method or means, for example.

Generally, the terms "stain" and "dye" may be used interchangeably herein. These terms may refer to a molecule capable of absorbing light of a wavelength in a spectral range of wavelengths from about 200 nm to about 1,200 nm, inclusive, for example, such as from about 250 nm to about 1,200 nm, inclusive, for example. Generally, a difference between an excitation maximum and an emission maximum associated with a stain or a dye may be referred to as a Stokes shift.

Generally, the term "luminescence" may refer to emission of light due to relaxation of a molecule from any electronically excited state to a ground state. Generally, the term "fluorescence" may refer to emission of light due to the relaxation of a molecule from an excited singlet state to a grounded singlet state. In either case, the excited state may be the result of excitation by light. The term luminescence encompasses the term fluorescence, as fluorescence is merely one subtype of luminescence. A metal complex may be associated with complex electronic transitions. In general, light emission from a metal complex may be referred to as luminescence. As used herein, luminescence and fluorescence, and associated terminology (such as luminescent and fluorescent, for example), are used interchangeably. Herein, luminescent and fluorescent may be used to refer to the capability of a material or composition, such as a metal complex, for example, to exhibit luminescence or fluorescence under suitable conditions, such as exposure to excitation, for example.

A luminescent metal complex, a composition, a solution, a kit, and/or a method described herein may be useful for a variety of purposes, such as staining poly(amino acids) in a sample and/or determining presence or absence of poly (amino acids) in a sample, for example. By way of example, a luminescent metal complex, such as one having low background luminescence in the absence of poly(amino acids), relatively greater luminescence in the presence of poly(amino acids), and/or relatively fast speed in the staining of poly (amino acids), such as immobilized proteins, peptides, and/or polypeptides, for example, may be useful in the detection of poly(amino acids). Further by way of example, a luminescent metal complex may be useful in the detection of poly(amino acids) in a gel matrix or on a membrane or otherwise associated with a medium, for example. Methods associated with a luminescent metal complex, such as methods of preparation or use thereof, for example, may also be useful. Useful luminescent metal complexes, and associated technology, such as methods of using same, for example, are described herein. Same may be discussed in the context of applications involving poly(amino acids) merely by way of example, not limitation.

Poly(amino acids), such as proteins or polypeptides, or a sample comprising same, may be associated with any of a variety of environments. By way of example, poly(amino acids), or a sample comprising same, may be associated with a dead cell, a live cell, a biological fluid, and/or the like. Further by way of example, poly(amino acids), or a sample comprising same, may be associated with a gel, such as a gel comprising agarose, acrylamide, and/or polyacrylamide, for example, a surface, such as a membrane comprising nitrocellulose, nylon, and/or poly(vinylidene difluoride), for example, or other media. Still further by way of example, poly(amino acids), or a sample comprising same, may be associated with a gel or a gel matrix, such as a polyacrylamide gel matrix associated with SDS-PAGE, for example, or a surface, a semi-solid surface, or a solid surface, such as a membrane surface associated with western blot, for example.

Poly(amino acids), or a sample comprising same, such as any in any of a variety of environments, for example, may be subjected to an electrophoretic process. The electrophoretic process may be sufficient to separate poly(amino acids), such as poly(amino acids) present in a sample, for example. Poly (amino acids), or a sample comprising same, such as any in any suitable environment, for example, may be exposed to an appropriate luminescent metal complex, or a solution comprising same, sufficient to stain poly(amino acids). The exposure may be sufficient to stain poly(amino acids), such as poly(amino acids) present in a sample, for example, in any suitable manner, such as any described herein. The exposure may be for any suitable amount of time, such as up to at least about five minutes, up to at least about thirty minutes, or up to at least about ninety minutes, for example. The exposure may precede electrophoretic processing of poly(amino acids), or a sample comprising same, may be at least partially concurrent with such electrophoretic processing, and/or may follow such electrophoretic processing.

A sample that does not comprise poly(amino acids) may be associated with the above-described environments and/or may be processed in any above-described manner, as may be the case when a sample is being studied or tested to determine whether or not it comprises poly(amino acids), for example. If a sample does not contain poly(amino acids), it would fail to exhibit separation of poly(amino acids) upon electrophoretic processing, and would fail to exhibit staining of poly(amino acids) upon exposure to an appropriate luminescent metal complex, with any such failure indicating that the sample does not contain poly(amino acids).

A method of processing a sample may thus comprise exposing the sample to a solution sufficient to stain poly (amino acids) of the sample, if present, wherein the solution comprises at least one luminescent complex, such as any described herein. A method of determining presence or absence of poly(amino acids) in a sample may comprise exposing the sample as just described and detecting stained poly(amino acids) of the sample, if present, or a lack thereof, if absent. Some luminescent complexes and associated technology (such as compositions, solutions, and kits) useful in methods such as these, for example, are now described.

A luminescent metal complex, such as that appropriate for the exposure described above, for example, may comprise a transition metal, at least one ligand sufficient to render the complex relatively lipophilic, and at least one counter ion. The net charge of a luminescent metal complex, excluding any counter ion(s), may be positive. A number of counter ion(s) may be sufficient to balance the net charge of the luminescent metal complex and thereby render the luminescent metal complex balanced or neutral in terms of charge. The counter ion(s) may be any suitable counter ion(s), such as any sufficient to render the luminescent metal complex sufficiently soluble or any compatible with the solubility of the metal complex. Merely by way of example, a luminescent metal complex may be associated with a solubility of at least about 0.05 µM, or at least about 5 µM, relative to a solution, such as an aqueous solution or a staining solution described herein, for example.

The transition metal of the luminescent metal complex may be selected from ruthenium (II), rhenium(I), palladium (II), platinum(II), europium(III), and terbium(III). The at least one ligand sufficient to render the complex relatively lipophilic may comprise one ligand that is itself so sufficient, or a combination of ligands that are together so sufficient. The at least one ligand sufficient to render the complex relatively lipophilic may be selected from a monodentate heterocyclic nitrogen ligand, a bidentate heterocyclic nitrogen ligand, and a tridentate heterocyclic nitrogen ligand, such as any of same or any combination of same that is relatively lipophilic, for example. The at least one ligand sufficient to render the complex relatively lipophilic may be selected from any of a number of appropriately substituted ligands. By way of example, the at least one ligand sufficient to render the complex relatively lipophilic may be selected from a substituted pyridine, a substituted 2,2'-bipyridine, a substituted 1,10-phenanthroline, and a substituted 2,2':6',2"-terpyridine, for example.

The luminescent metal complex may comprise ligands other than the at least one ligand sufficient to render the complex relatively lipophilic that was just described. Such other ligands, if any, may or may not be relatively lipophilic or may or may not be sufficient to render the complex relatively lipophilic. Such other ligands, if any, may be selected from a monodentate heterocyclic nitrogen ligand, a bidentate heterocyclic nitrogen ligand, and a tridentate heterocyclic nitrogen ligand. Such other ligands, if any, may be selected from pyridine, a substituted pyridine, 2,2'-bipyridine, a substituted 2,2'-bipyridine, 1,10-phenanthroline, a substituted 1,10-phenanthroline, 2,2':6',2"-terpyridine, and a substituted 2,2':6',2"-terpyridine.

An example of a useful luminescent metal complex may be one that comprises a transition metal, such as any described herein, and any heterocyclic nitrogen ligand or combination thereof, such as any of same described herein, wherein at least one ligand is sufficient to render the complex relatively lipophilic, and at least one counter ion. An example of a useful composition, solution, or kit may be one that comprises a luminescent metal complex, such as any of same described herein. An example of a useful method may be one that employs a luminescent metal complex, or a composition, solution, or kit comprising same, in a useful manner, such as any described herein.

A luminescent metal complex, such as that appropriate for the exposure described above, for example, may be represented by a structural formula, such as that (Formula 1) set forth below.

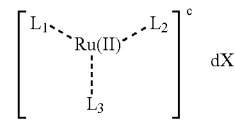

Formula 1

In some embodiments $L_1$ is a ligand selected from 2,2'-bipyridine, a neutrally-substituted 2,2'-bipyridine comprising less than 23 carbon atoms, 1,10-phenanthroline, and a neutrally substituted 1,10-phenanthroline comprising less than 25 carbon atoms. In some embodiments, $L_2$ is a ligand selected from 2,2'-bipyridine, a neutrally-substituted 2,2'-bipyridine comprising less than 23 carbon atoms, 1,10-phenanthroline, and a neutrally substituted 1,10-phenanthroline comprising less than 25 carbon atoms. $L_1$ and $L_2$ may be the same or may be different. In some embodiments, $L_3$ is a ligand selected from a substituted 2,2'-bipyridine and a substituted 1,10-phenanthroline.

At least one ligand selected from ligand $L_1$, ligand $L_2$, and ligand $L_3$ may be sufficient to render the complex relatively lipophilic. By way of example, such a ligand or ligands may be relatively lipophilic or may comprise at least one substituent that may be relatively lipophilic, such as in a manner described herein, for example, such that the metal complex is relatively lipophilic. At least one of the ligands selected from ligand $L_1$, ligand $L_2$, and ligand $L_3$ may be sufficient to interact or capable of interacting with poly(amino acids), such as in a manner described herein, may be sufficient to render the luminescent metal complex sufficient to stain or capable of staining poly(amino acids), such as in a manner described herein, may be sufficient to render the luminescent metal complex sufficient to detect and/or identify or capable of detecting and/or identifying poly(amino acids), such as in a manner described herein, and/or the like. Such a luminescent metal complex may comprise a charge, c, of 1+ or 2+; a counter ion or an anion, X; and a number, d, of counter ion(s) or anion(s) X, such as that sufficient to balance or to neutralize the charge, c, for example. In Formula 1, the charge, c, may be recognized as a "net charge" of the complex exclusive of its counter ion(s), dX, in the manner described above. The anion(s) X may be any suitable anion(s), such as any sufficient to render the metal complex sufficiently soluble or any compatible with the solubility of the metal complex.

For complexes of Formula 1, $L_1$, $L_2$, and $L_3$ are unsubstituted or substituted with a total of no more than two negatively charged sulfonate groups combined such that net charge c is not negative, i.e. it can be neutral (O), or charged positively (e.g. 1+ or 2+). The sulfonate substituents may be present on any of $L_1$, $L_2$, and $L_3$ providing that there are no more than two negatively charged sulfonate groups combined in the complex of Formula 1. In some embodiments of the invention, the number of sulfonate groups, if present in $L_1$, $L_2$, and $L_3$, combined is 1. In some embodiments of the invention, the number of sulfonate groups, if present in $L_1$, $L_2$, and $L_3$, combined is 0.

In some embodiments, $L_1$ is a ligand selected from 2,2'-bipyridine, 4,4'-dimethyl-2,2'-bipyridine, 3,4,3',4'-tetramethyl-2,2'-bipyridine, 4,4'-diphenyl-2,2'-bipyridine, 1,10-phenanthroline, 4-methyl-1,10-phenanthroline, 5-methyl-1, 10-phenanthroline, 4,7-dimethyl-1,10-phenanthroline, 5,6-dimethyl-1,10-phenanthroline, 3,4,7,8-tetramethyl-1,10-phenanthroline, 5-phenyl-1,10-phenanthroline, bathophenanthroline, and 5-chloro-1,10-phenanthroline, any of which is unsubstituted or substituted with one sulfonate group, providing that the condition of a total of no more than two negatively charged sulfonate groups combined in the complex of Formula 1 is met. In some embodiments, $L_2$ may be a ligand selected from 2,2'-bipyridine, 4,4'-dimethyl-2,2'-bipyridine, 3,4,3',4'-tetramethyl-2,2'-bipyridine, 4,4'-diphenyl-2,2'-bipyridine, 1,10-phenanthroline, 4-methyl-1,10-phenanthroline, 5-methyl-1,10-phenanthroline, 4,7-dimethyl-1,10-phenanthroline, 5,6-dimethyl-1,10-phenanthroline, 3,4,7,8-tetramethyl-1,10-phenanthroline, 5-phenyl-1,10-phenanthroline, bathophenanthroline, and 5-chloro-1,10-phenanthroline, any of which is unsubstituted or substituted with one sulfonate group, providing that the condition of a total of no more than two negatively charged sulfonate groups in the complex of Formula I is met.

In some embodiments, $L_3$ may be 4,4'-dinonyl-2,2'-bipyridine. In some embodiments, $L_3$ may be bathophenanthroline.

In some embodiments, $L_3$ may be a ligand represented by a structural formula, such as that (Formula 2) set for the below.

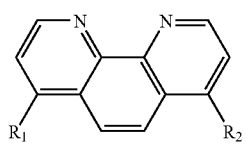

Formula 2

In such a case, $R_1$ may be —H, phenyl, or sulfophenyl; and $R_2$ may be a C6 to C22 alkyl, the alkyl optionally comprising at least one hetero atom selected from halogen, nitrogen, oxygen, and sulfur; a phenyl, substituted with a C1 to C18 alkylaminosulfo substituent, wherein the alkyl thereof is linear or branched and optionally comprises an aryl and/or at least one oxygen atom; or a phenyl, substituted with a C2 to C24 dialkylaminosulfo substituent, wherein the dialkyl thereof is linear or branched, optionally comprises an aryl and/or at least one oxygen atom, and optionally forms a saturated or unsaturated, substituted or unsubstituted, 4- to 7-membered ring. In such embodiments, $L_3$ may be referred to as a substituted 1,10-phenanthroline. When $R_1$ is —H or phenyl, c may be 2+. When $R_1$ is sulfophenyl, c may be 1+.

In some embodiments, at least one ligand selected from ligand $L_1$ and ligand $L_2$ may be 1,10-phenanthroline; c may be 2+; $R_1$ may be —H; and $R_2$ may be represented by the formula, —$(CH_2)_4NHCOR_3$, wherein $R_3$ may be a $C_7$ to $C_{17}$ alkyl. In some embodiments, at least one ligand selected from ligand $L_1$ and ligand $L_2$ may be bathophenanthroline; c may be 1+; $R_1$ may be sulfophenyl; and $R_2$ may be represented by the formula, —$ArSO_2NR_4R_5$, wherein $R_4$ may be —H or a C1 to C7 alkyl; $R_5$ may be —H or a C1 to C7 alkyl; and optionally $R_4$ and $R_5$ in combination may form a C4- to C7-membered ring, wherein optionally, the ring may be substituted once by a methyl or an ethyl, or twice by a methyl, twice by an ethyl, or twice, once by a methyl and once by a ethyl. In the latter embodiments, any suitable substitution position for the sulfonate group and any suitable substitution position for the sulfonamide group may be employed.

An example of a useful luminescent metal complex is any of same that may be associated with Formula 1 and/or Formula 2 above. An example of a useful composition, solution, or kit may be one that comprises a luminescent metal complex, such as any of same described herein. An example of a useful method may be one that employs a luminescent metal complex, or a composition, solution, or kit comprising same, in a useful manner, such as any described herein.

A solution comprising a luminescent metal complex, such as any described herein, for example, may have any of a variety of useful applications, such as staining, detecting, and/or identifying applications, such as any of those described herein, for example. The luminescent metal complex may comprise at least one counter ion. The luminescent metal complex, exclusive of its counter ion(s), may be associated with a net charge that is positive. The luminescent metal complex, inclusive of its counter ion(s), may be associated with a charge that is neutral. The luminescent metal complex may comprise a transition metal, such as any of those previously described (such as rhenium (I) or ruthenium (II), merely by way of example), and at least one ligand sufficient to render the luminescent metal complex relatively lipophilic, such as any described herein.

A concentration of the luminescent metal complex in a solution may be from about 0.05 µM to about 5 µM, inclusive, relative to the solution. Such a solution may be aqueous. Such a solution may comprise at least one water-miscible solvent, for example. A suitable water-miscible solvent may be an organic solvent sufficient to form a homogeneous solution when mixed with water at a solvent:water volume ratio of from at least about 5:95 to about 1:1, inclusive, such as from about 1:4 to about 1:1, inclusive, for example. A suitable water-miscible solvent may comprise methanol, ethanol, 1,2-propanediol, ethylene glycol, and/or glycerol, for example. Such a solution may comprise at least one component selected from an acid, a buffering agent, an inorganic salt, a metal-chelating agent, a detergent, a reducing agent, and/or an agent for facilitating staining and/or for facilitating reduction of background. A suitable acid may comprise an organic acid, for example, such as acetic acid, lactic acid, formic acid, phosphoric acid, and/or other relatively weak acid(s), for example. A suitable buffering agent may comprise tris(hydroxymethyl)methylamine (Tris), any suitable known biological buffer, and/or the like, for example. A suitable inorganic salt may comprise a salt that comprises a divalent ion, such as magnesium chloride or ammonium sulfate, for example. A suitable metal-chelating agent may comprise ethylenediamine tetraacetic acid (EDTA), ethylene glycol bis-(β-aminoethyl ether)tetraacetic acid (EGTA), and/or the like. A suitable detergent may comprise a neutral detergent, such as TWEEN 20 (Sigma-Aldrich Corporation of St. Louis, Mo.) or Pluronic F-127 (Sigma-Aldrich Corporation of St. Louis, Mo.), for example, and/or the like. A suitable reducing agent may comprise dithiothreitol (DTT), ascorbic acid, and/or tricarboxyethylphosphine (TCEP), for example. A suitable agent for facilitating staining and/or for facilitating reduction of background may comprise a neutral agent, such as TWEEN 20 (Sigma-Aldrich Corporation of St. Louis, Mo.) or Pluronic F-127 (Sigma-Aldrich Corporation of St. Louis, Mo.), for example, and/or the like. A suitable solution may comprise TWEEN 20 at a concentration of from about 0.01% to about 0.1% by volume, inclusive, relative to the solution. A suitable solution may comprise Pluronic F-127 at a concentration of from about 0.01% to about 1.5% by volume, inclusive, relative to the solution. Additional examples of possible components may be found elsewhere herein, such as in the Examples, merely by way of example.

An example of a useful solution may be one comprising at least one luminescent complex, such as any described herein, at a concentration of about 0.05 μM to about 5 μM, inclusive, relative to the solution, such as about 0.05 μM to about 3.5 μM, inclusive, relative to the solution, for example. The solution may comprise at least one water-miscible organic solvent at any suitable concentration, such as at a concentration of about 0.1% to about 10% by volume, inclusive, relative to the solution. Merely by way of example, the organic solvent may be methanol. The solution may comprise at least one component selected from an acid, a buffering agent, an inorganic salt, a metal-chelating agent, a detergent, and/or a reducing agent, as described above, at any suitable concentration. Merely by way of example, the at least one component may comprise an organic acid, such as acetic acid and/or lactic acid, for example, at a concentration of about 0.1% to about 3% by volume, inclusive, relative to the solution.

Another example of a useful solution may be one comprising at least one luminescent complex, such as any described herein, at a concentration of about 0.05 μM to about 5 μM, inclusive, relative to the solution, such as about 0.1 μM to about 3.5 μM, inclusive, relative to the solution, for example. The solution may comprise at least one water-miscible organic solvent at any suitable concentration, such as at a concentration of about 15% to about 40% by volume, inclusive, relative to the solution. Merely by way of example, the organic solvent may be methanol. The solution may comprise at least one component selected from an acid, a buffering agent, an inorganic salt, a metal-chelating agent, a detergent, and/or a reducing agent, as described above, at any suitable concentration. The solution may comprise an agent that is suitable or sufficient for reducing, or facilitates the reduction of, background in the detection of poly(amino acids). Merely by way of example, the at least one component may comprise an organic acid, such as acetic acid and/or lactic acid, for example, and may be at a concentration of about 5% to about 20% by volume, inclusive, relative to the solution. Merely by way of example, the at least one component may comprise a detergent, such as Pluronic F-127, for example, at a concentration of about 0.01% to about 1.5% by volume, inclusive, relative to the solution. A solution such as that just described, may be used to stain poly(amino acids) associated with a separation process, such as an electrophoretic process, for example, wherein poly(amino acids) do not need to be fixed beforehand.

A kit comprising a luminescent metal complex, such as any described herein, for example, or a solution, such as any described herein, for example, may have any of a variety of useful applications, such as staining, detecting, and/or identifying applications, such as any of those described herein, for example. Such a kit may comprise information, such as any concerning an application or a use of the complex, the solution, or the kit, such as any described herein, for example. Such a kit may comprise at least one agent suitable or sufficient for such an application or a use or for facilitating same, such as a buffer, a protein ladder, agarose acrylamide, polyacrylamide, for example, and/or the like.

A luminescent metal complex may be or may be rendered relatively lipophilic, as described herein. A method of producing and/or designing a luminescent metal complex may comprise providing luminescent metal complex that is relatively non-lipophilic and modifying same to produce a luminescent metal complex that is relatively lipophilic. The method may comprise modifying at least one ligand of the ligands of the relatively non-lipophilic luminescent metal complex such that it comprises at least one substituent sufficient to render the luminescent metal complex relatively lipophilic. The method may comprise replacing or substituting at least one ligand of the ligands of the relatively non-lipophilic luminescent metal complex with at least one ligand sufficient to render the luminescent metal complex relatively lipophilic. A luminescent metal complex, such as a complex so produced, for example, may be capable of interacting with poly(amino acids) via hydrophobic interaction, and optionally, electrostatic interaction, such as in a manner described herein, for example. A luminescent metal complex so produced may be capable of staining, detecting, and/or identifying poly(amino acids), such as in a manner described herein, for example.

In terms of relative lipophilicity, a relatively lipophilic substituent may refer to a hydrocarbon moiety that may comprise at least one heteroatom selected from a halogen, nitrogen, oxygen, sulfur, and/or silicone. A relatively lipophilic substituent may be neutral in charge. A relatively lipophilic substituent may comprise at least one unsaturated bond, such as at least one double bond and/or at least one triple bond, for example. A relatively lipophilic substituent may be of any structure or any composition sufficient to render the substituent capable of imparting relative lipophilicity to the luminescent metal complex. Examples of a suitable relatively lipophilic substituent include any of the following: a straight alkyl, a branched alkyl, an unsaturated alkyl, a substituted aryl, and an unsubstituted aryl. In general, the degree, level, or strength of lipophilicity of the substituent may correspond with the number of carbon atom(s) associated with the substituent. For example, a substituent comprising a higher number of carbon atoms may generally be associated with greater lipophilicity. In general, the overall degree, level, or strength of lipophilicity of a luminescent metal complex may be correspond with the sum of the degrees or strengths of lipophilicity of each of the substituents, such as any relatively lipophilic substituent(s), for example, associated with the luminescent metal complex. A luminescent metal complex having a suitable or desirable degree, level, or strength of overall lipophilicity may comprise a suitable number of substituent(s) of relatively low lipophilic strength, a suitable number of substituent(s) of relatively moderate lipophilic strength, may comprise a suitable number of substituent(s) of relatively high lipophilic strength, or may comprise any mixture of substituent(s) of relatively low, moderate, and/or high lipophilic strength.

In general, a suitable level of lipophilicity, or suitable number of relatively lipophilic substituent(s) associated with a luminescent metal complex, may depend on the net charge of the luminescent metal complex exclusive of its counter ion(s). By way of example, if a luminescent metal complex exclusive of its counter ion(s) comprises a relatively high net positive charge, such as 2+ or 3+, for example, or a relatively high net negative charge, such as 2− or 3−, for example, at least one lipophilic substituent of at least one lipophilic ligand of the complex may comprise a relatively high number of carbon(s), such as about 8 to about 30 carbons, for example. Further by way of example, if a luminescent metal complex comprises exclusive of its counter ion(s) comprises a relatively low net charge, such as 1−, 0 or 1+, for example, at least one lipophilic substituent of at least one lipophilic ligand of the complex may comprise a relatively low number of carbon(s), such as from about 4 to about 12 carbons, for example. In general, a suitable number of substituent(s) of suitable lipophilicity may be employed to render a luminescent metal complex sufficiently lipophilic to stain poly(amino acids).

In general, any suitable luminescent metal complex, such as any described herein, may interact with poly(amino acids), such as to stain poly(amino acids), for example. The interaction may comprise hydrophobic interaction, which may be referred to as van der Waals interaction. Hydrophobic interaction may take place between a relatively lipophilic moiety or relatively lipophilic moieties of the complex and a relatively hydrophobic region or relatively hydrophobic regions of poly(amino acids). The interaction may comprise hydrophobic interaction, or hydrophobic interaction and electrostatic interaction. Electrostatic interaction may take place when the luminescent metal complex exclusive of any counter ion(s) is net charged, for example.

In terms of hydrophobic interaction, a luminescent metal complex may interact with hydrophobic regions of poly(amino acids). This may be referred to as direct hydrophobic interaction. A luminescent metal complex may interact with poly(amino acids) more indirectly, such as via an agent, a coating, and/or the like, that may be associated with the poly(amino acids). For example, when an agent, such as a detergent, for example, is used in connection with poly(amino acids), such as to denature and/or to coat the poly(amino acids), for example, a luminescent metal complex may interact with the agent, such as entering and/or partitioning into a lipid layer or a hydrophobic layer or a membrane layer of such an agent, for example. This may be referred to as indirect hydrophobic interaction. By way of example, an agent that may be associated with poly(amino acids) may be an SDS agent or detergent sufficient for denaturing and/or coating the poly(amino acids) in a process, such as a gel electrophoresis process. In such a case, a luminescent metal complex may enter or partition into a hydrophobic layer of the SDS agent or the detergent. A luminescent metal complex may interact with poly(amino acids) directly, such as in a manner described herein, for example, indirectly, such as in a manner described herein, for example, or both. A luminescent metal complex may interact with poly(amino acids) via electrostatic interaction, as mentioned above. Any of the above-mentioned interactions, or any suitable combination thereof, may result in the staining of the poly(amino acids).

In terms of electrostatic interaction, a luminescent metal complex may interact with poly(amino acids) via a charge or charges associated with the complex and a charge or charges associated with the poly(amino acids). Any such electrostatic interaction may be attractive or repulsive, as may be determined by one or more factors, such as the net charge associated with the luminescent metal complex exclusive of any counter ion(s), the pH of a solution comprising the luminescent metal complex, and/or presence or absence of an agent or a detergent, such as SDS, for example, in association with the poly(amino acids), such as on a surface of the poly(amino acids), for example. For example, in general, if the pH of a solution comprising a luminescent metal complex is acidic, poly(amino acids), such as proteins, exposed to the solution may become positively charged, such as via protonation of any lysine side chain(s) and/or any arginine side chain(s), for example. In such a case, if there is no agent or detergent, such as SDS, for example, associated with the poly(amino acids), the positively charged poly(amino acids) and a luminescent metal complex that, exclusive of any counter ion(s), is associated with a net positive charge, may electrostatically repulse one another. Further, a luminescent metal complex that is more lipophilic than another luminescent metal complex may sufficient to overcome, or comparatively better at overcoming, any such repulsive electrostatic interaction, and may thus be sufficient to stain, or comparatively better at staining, the poly(amino acids). Further by way of example, if there is an agent or a detergent, such as SDS, for example, which is negatively charged, associated with the poly(amino acids), such as on a surface of the poly(amino acids), for example, there may be an overwhelming amount of negative charges associated with the poly(amino acids). In such a case, the negatively charged poly(amino acids) and a luminescent metal complex that, exclusive of any counter ion(s), is associated with a net positive charge, may electrostatically attract one another. A luminescent metal complex that is less lipophilic than another luminescent metal complex may be sufficient to stain, or comparatively better at staining, the poly(amino acids).

A luminescent metal complex, such as any described herein, may be used to stain and/or to detect poly(amino acids), such a proteins, for example, immobilized in a gel matrix. Staining may precede, follow, or be at least partially concurrent with electrophoretic separation of the poly(amino acids), such as via SDS-PAGE, for example. Staining of the poly(amino acids) may be carried out by incubating a medium, such as a gel, for example, that is associated with the separated proteins, in a solution that comprises a luminescent metal complex, such as any such solution described herein. The incubation may be carried out at any suitable temperature, such as from about 4° C. to about 45° C., inclusive, such as around room temperature, for example. An example of a suitable solution may be one that comprises a luminescent metal complex, such as any described herein, at a concentration of about 0.1 µM to about 3.5 µM, inclusive, relative to the solution, methanol at a concentration of about 15% to about 40% by volume, inclusive, relative to the solution, and a neutral detergent at a concentration of about 0.01% to about 1.5% by volume, inclusive, relative to the solution, merely by way of example. Optionally, the medium may be exposed to an agent that is suitable or sufficient for reducing, or facilitates the reduction of, background in the detection of poly(amino acids). Such an agent may be employed as part of the solution used for staining, or before, at least partially concurrent with, and/or after exposure to the solution used for staining. Merely by way of example, such an agent may comprise water and/or an aqueous solution. Merely by way of example, such an aqueous solution may comprise an organic solvent and/or an acid. Once the poly(amino acids) are stained, they may be visualized or detected via any suitable means, such as an ultraviolet (UV) transilluminator, a Dark Reader from Clare Chemical Research, Inc. (Dolores, Colo.), a laser-based gel scanner, and/or the like, for example.

A screening process may be used to determine or to assess relative lipophilicity associated with a luminescent metal complex. By way of example, a luminescent metal complex may be screened using any staining method described herein. Further by way of example, a number of luminescent metal complexes, such as closely associated complexes, for example, associated with various levels of lipophilicity, may be screened using any staining method described herein. Merely by way of example, such closely associated complexes may comprise complexes that are relatively similar in structure, but differ in terms of the level of lipophilicity associated with at least one of the ligands. In such a case, different luminescent metal complexes of varying lipophilicity, such as those comprising the same transition metal but at least one different relatively lipophilic ligand, for example, may be prepared or provided and used in a staining method described herein. In general, a luminescent metal complex that performs better relative to another luminescent metal complex in such a staining method, such as one that more clearly or more quickly shows stained poly(amino acids), for example, has a relatively greater degree of lipophilicity. It may be desirable to consider, and perhaps balance, an appropriate degree of lipophilicity associated with the complex and an appropriate size associated with the complex. Merely by way of example, a complex having very high lipophilicity may be very large in size, which may reduce staining speed, for example.

In general, a luminescent metal complex may be better than or superior to an organic dye in terms of performance in the staining of poly(amino acids), such as proteins or peptides, for example. This may be the case in particular staining applications, such as the staining of poly(amino acids) associated with a gel, for example. Such better or superior performance associated with a luminescent metal complex, relative to performance associated with an organic dye, may be associated with a Stokes shift of the luminescent metal complex, which may be large relative to that associated with an organic dye. By way of example, Complex No. 4 of Table 1 may be associated with a Stokes shift of about 160 nm, as may be determined from FIG. 5, while an organic dye may be associated with a Stokes shift of less than 30 nm or less than 20 nm. In general, in the staining of poly(amino acids), such as proteins associated with a gel, for example, a luminescent metal complex associated with a suitable Stokes shift, such as a relatively large Stokes shift, for example, may be associated with lowering or minimizing quenching of luminescence. By way of illustration, at high concentration, a luminescent stain that is associated with a relatively small Stokes shift may have a high tendency to quench its own luminescence. This may be attributed to the absorption of light emission of one molecule of the stain by another molecule, such as a neighboring molecule, for example, of the stain. As such, in the staining of poly(amino acids), wherein stain molecules may be highly concentrated on the surface of the poly(amino acids), luminescence associated with such a small-Stokes shift stain may be quenched. A luminescent metal complex, such as any described herein, may be associated with a more suitable Stokes shift, such as a relatively large Stokes shift, and thus may be associated with less luminescent quenching.

A luminescent metal complex may be better than or superior to an organic dye in terms of performance in the staining of poly(amino acids), such as proteins or peptides, for example, in other ways. By way of example, in general, in the staining of poly(amino acids), such as proteins associated with a gel, for example, a luminescent metal complex associated with a suitable Stokes shift, such as a relatively high Stokes shift, may be associated with a relatively wide linear detection range. Further by way of example, in general, in the staining of poly(amino acids), such as proteins associated with a gel, for example, a luminescent metal complex may be associated with a relatively long luminescence lifetime. This aspect of the complex may permit what may be referred to as time-resolved luminescence imaging. In general, in such a staining application, a luminescent metal complex may be associated with poly(amino acid) detection of relatively high sensitivity.

Previously, a metal complex used in protein-staining applications, exclusive of its counter ion(s), was typically associated with a net charge that was negative. (See U.S. Pat. No. 6,316,267, for example.) Typically, such a metal complex comprised multiple negative charges and stained proteins via electrostatic interaction or attraction between the negative charge(s) associated with the complex and positive charge(s) associated with groups, such as protonated lysine and/or arginine side chains, for example, associated with the proteins. It is noted that following SDS-PAGE, proteins that were embedded in a gel were typically fixed before they were stained. The fixation process typically took place under acidic conditions, such that the proteins so fixed were for the most part positively charged.

A luminescent metal complex, such as any described herein, that, exclusive of its counter ion(s), has a net charge that is positive, may be employed in poly(amino acid)-staining applications, such as protein-staining applications involving a gel, for example. Such a luminescent metal complex may be better than or superior to a metal complex that, exclusive of its counter ion(s), has a net charge that is negative, in terms of performance in the staining of poly(amino acids), such as proteins or peptides, for example.

In Example 15, for example, the performance of a luminescent metal complex described herein, namely, Complex No. 17 of Table 1, in a protein-staining application, and the performance of a commercially available metal complex, namely, the commercially available SYPRO Ruby complex, in a protein-staining application were determined. Complex No. 17 of Table 1 is a ruthenium complex that, exclusive of its counter ion, is positively net charged. The SYPRO Ruby complex is a ruthenium complex comprising negatively charged sulfonate groups that render the complex, exclusive of its counter ion(s), negatively net charged under staining conditions. The results of Example 15 are shown in FIG. 1.

As shown in FIG. 1, a luminescent metal complex described herein, such as Complex No. 17 of Table 1, for example, may be capable of staining proteins in a relatively short amount of time, such as less or even well less than about two hours, for example, may be capable of leading to the detection of proteins at a concentration of as little as about 1 nanogram or less in a sample, may be associated with relatively low background (for example, relatively dark background, relatively free of white or gray or cloudy noise, in the photographs, such that the white or gray foreground bands are relatively clear), and may be capable of providing suitable detection results without an additional destaining process. A luminescent metal complex described herein may take as little as about 30 minutes or less, such as about 15 minutes, for example, to achieve suitable to excellent staining and/or detection results, as can be seen in FIG. 1. As in Example 15, when a luminescent metal complex described herein, such as Complex No. 17 of Table 1, for example, is used in a protein-staining application, fixation and staining may be combined. Such a combination may take about 1.5 hours or less.

As also shown in FIG. 1, a prior metal complex, such as the commercially available SYPRO Ruby complex, for example, may take a comparatively long amount of time, such as overnight, to stain proteins with a reasonable level of sensitivity, may be associated with relatively high background (for example, white or gray or cloudy noise in the background of the photographs, such that the white or gray foreground bands are somewhat or relatively obscure), and may, because of associated background, require an additional destaining process, such as a 30-minute destaining process. As in Example 15, when a prior metal complex, such as the commercially available SYPRO Ruby complex, for example, is used in a protein-staining application, it may be necessary to employ a separate fixation process prior to the staining process, and thus, overall process time may be relatively increased or extended.

As described herein, a luminescent metal complex may comprise a transition metal and at least one ligand. The transition metal may be any of the transition metals described herein, such as Ru(II), for example. The at least one ligand may comprise a combination of heterocyclic nitrogen ligands. A suitable heterocyclic nitrogen ligand may be a monodentate heterocyclic nitrogen ligand, a bidentate heterocyclic nitrogen ligand, or a tridentate heterocyclic nitrogen ligand. At least one of the ligands may be sufficient to render the luminescent metal complex relatively lipophilic, or to render the luminescent metal complex capable of staining poly(amino acids) in any suitable manner, such a via hydrophobic interaction and optionally electrostatic interaction.

When the luminescent metal complex comprises the transition metal, Ru(II), it may further comprise six nitrogen atoms sufficient to coordinate with the transition metal and form an octahedrally structured complex, which may be relatively stable. The six nitrogen atoms may come from a number of sources, such as monodentate ligand(s), polydentate ligand(s), or a combination thereof, for example. Merely by way of example, such sources may comprise: six monodentate ligands; four monodentate ligands and one bidentate ligand; two monodentate ligands and two bidentate ligands; three bidentate ligands; three monodentate ligands and one tridentate ligand; and two tridentate ligands. Merely by way of example, a suitable monodentate ligand may be selected from a pyridine and a substituted pyridine. Merely by way of example, a suitable bidentate ligand may be selected from a 2,2'-bipyridine, a substituted 2,2'-bipyridine, a 1,10-phenanthroline, and a substituted 1,10-phenanthroline. Merely by way of example, a suitable tridentate ligand may be selected from a 2,2':6',2"-terpyridine and a substituted 2,2':6',2"-terpyridine. An example of a suitable ruthenium-comprising complex has been described herein in connection with Formula 1 above. An example of a suitable suitable ruthenium-comprising complex has been described herein in connection with Formula 1 and Formula 2, as well.

Preparation of a Luminescent Metal Complex May be Via any Suitable Method, Such as Via any Suitable, Previously known method, for example. Any suitable ligand, such as those described herein, may be involved in any such preparation of a luminescent metal complex. Examples of a suitable ligand include the following: a phosphine, a phosphate, carbon monoxide, cyanide, and an aromatic, nitrogen-comprising heterocylic compound, such as pyridine, imidazole, 2,2'-bipyridine, 1,10-phenanthroline, terpyridine, pyrazine, or any substituted derivative thereof, for example. A suitable ligand may be commercially available or may be prepared via any suitable method, such as via any suitable, previously known method, for example. Any suitable combination of ligands may be employed.

Preparation of a Luminescent Metal Complex May Comprise Providing or Starting with a Metal Complex that May comprise at least one relatively labile ligand, such as a halide and/or carbon monoxide. A suitable ligand may be provided under suitable conditions, such as in a suitable solvent in an inert atmosphere, such as nitrogen or argon, for example. The metal complex may be exposed to this ligand and heated under conditions sufficient to initiate a ligand-substitution reaction, where the suitable ligand just described replaces at least one labile ligand. If a luminescent metal complex is to comprise more than one type of ligand, a first type of ligand may be added in a first ligand-substitution reaction, a second type of ligand may be added in a second substitution reaction, as so on, until the desired luminescent metal complex is formed. A luminescent ruthenium complex may comprise aromatic nitrogen heterocyclic ligands, for example. A luminescent rhenium complex may comprise a mixture of at least one carbon monoxide ligand and at least one aromatic nitrogen-comprising heterocyclic ligand, for example. A luminescent terbium complex or a luminescent europium complex may comprise at least one negatively charged chelating ligand, for example.

A luminescent metal complex comprising a transition metal may be prepared in a different manner, such as via a different ligand-substitution reaction scheme or method or a different ligand-assembly scheme or method, than a manner that may be used to prepare a different luminescent metal complex. A suitable manner, scheme or method may be used in order to achieve suitable-to-optimal luminescence quantum yield for a particular metal luminescent metal complex. Upon completion of ligand substitution or ligand assembly, crude product may be purified by chromatography, recrystallization, and/or any suitable purification method or means, such as any previously known method or means, for example.

Synthesis of a Luminescent Ruthenium Complex

A luminescent ruthenium complex may be prepared as now described, merely by way of example. For example, a luminescent ruthenium complex may be prepared by attaching a relatively lipophilic substituent to a reactive group (—NH$_2$) of a ruthenium complex (commercially available from Biotium, Inc. of Hayward, Calif.), in any suitable manner, such as that shown in Scheme 1 below. A suitable preparation scheme for another luminescent ruthenium complex is also shown in Scheme 1 below.

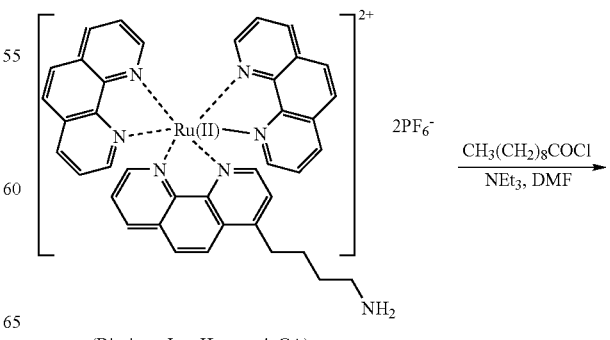

Scheme 1

(Biotium, Inc. Hayward, CA)

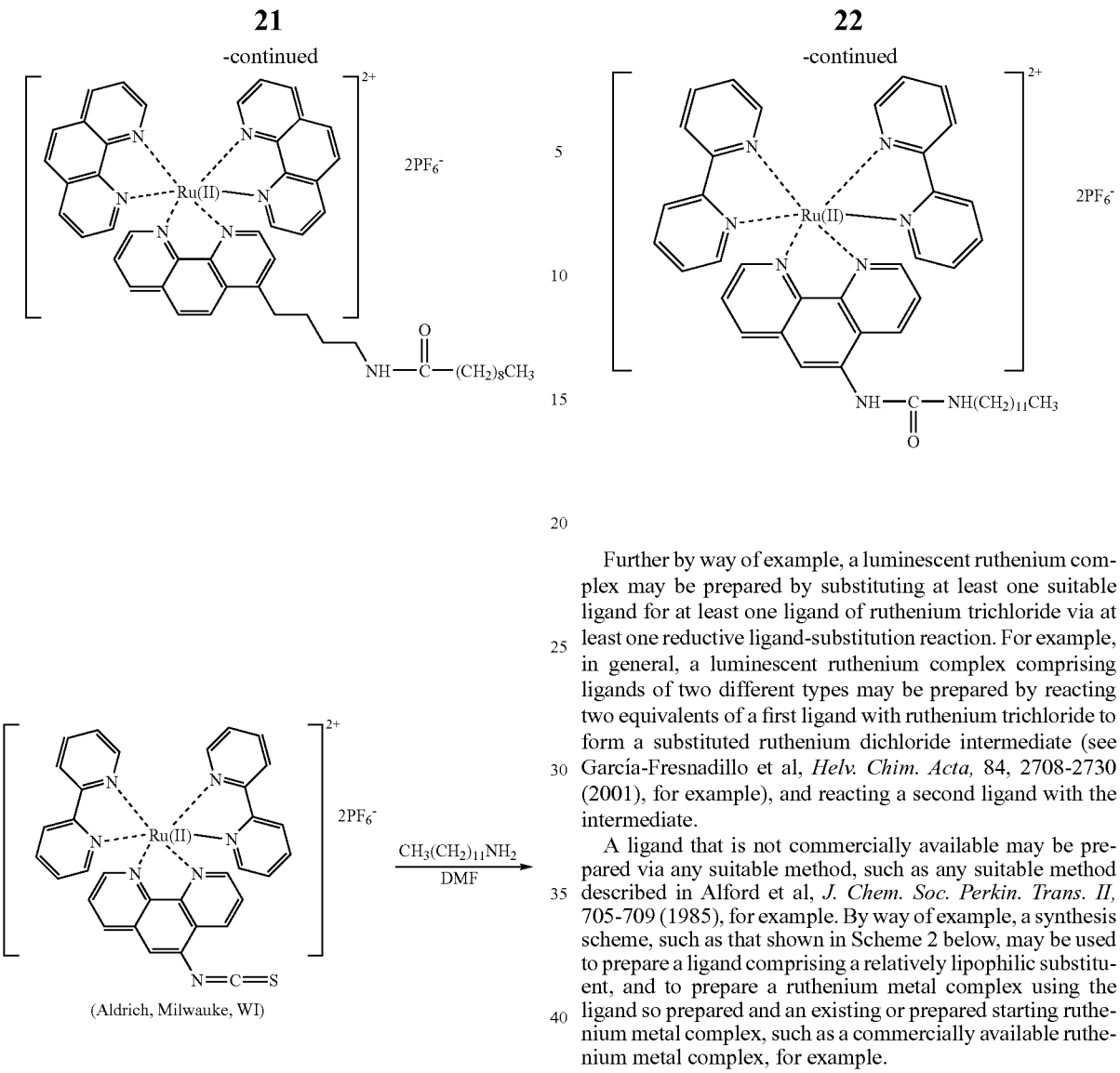

Further by way of example, a luminescent ruthenium complex may be prepared by substituting at least one suitable ligand for at least one ligand of ruthenium trichloride via at least one reductive ligand-substitution reaction. For example, in general, a luminescent ruthenium complex comprising ligands of two different types may be prepared by reacting two equivalents of a first ligand with ruthenium trichloride to form a substituted ruthenium dichloride intermediate (see García-Fresnadillo et al, *Helv. Chim. Acta,* 84, 2708-2730 (2001), for example), and reacting a second ligand with the intermediate.

A ligand that is not commercially available may be prepared via any suitable method, such as any suitable method described in Alford et al, *J. Chem. Soc. Perkin. Trans. II,* 705-709 (1985), for example. By way of example, a synthesis scheme, such as that shown in Scheme 2 below, may be used to prepare a ligand comprising a relatively lipophilic substituent, and to prepare a ruthenium metal complex using the ligand so prepared and an existing or prepared starting ruthenium metal complex, such as a commercially available ruthenium metal complex, for example.

Scheme 2

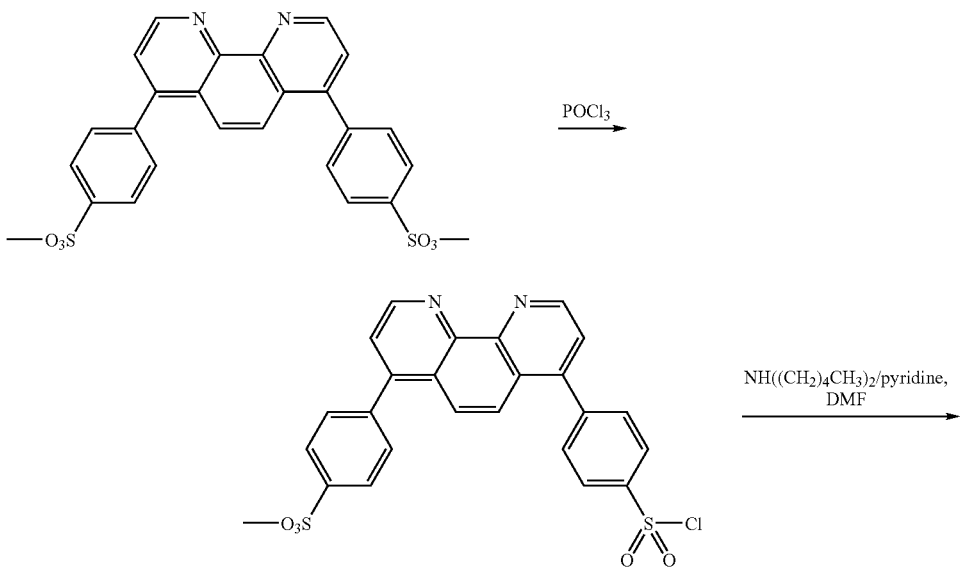

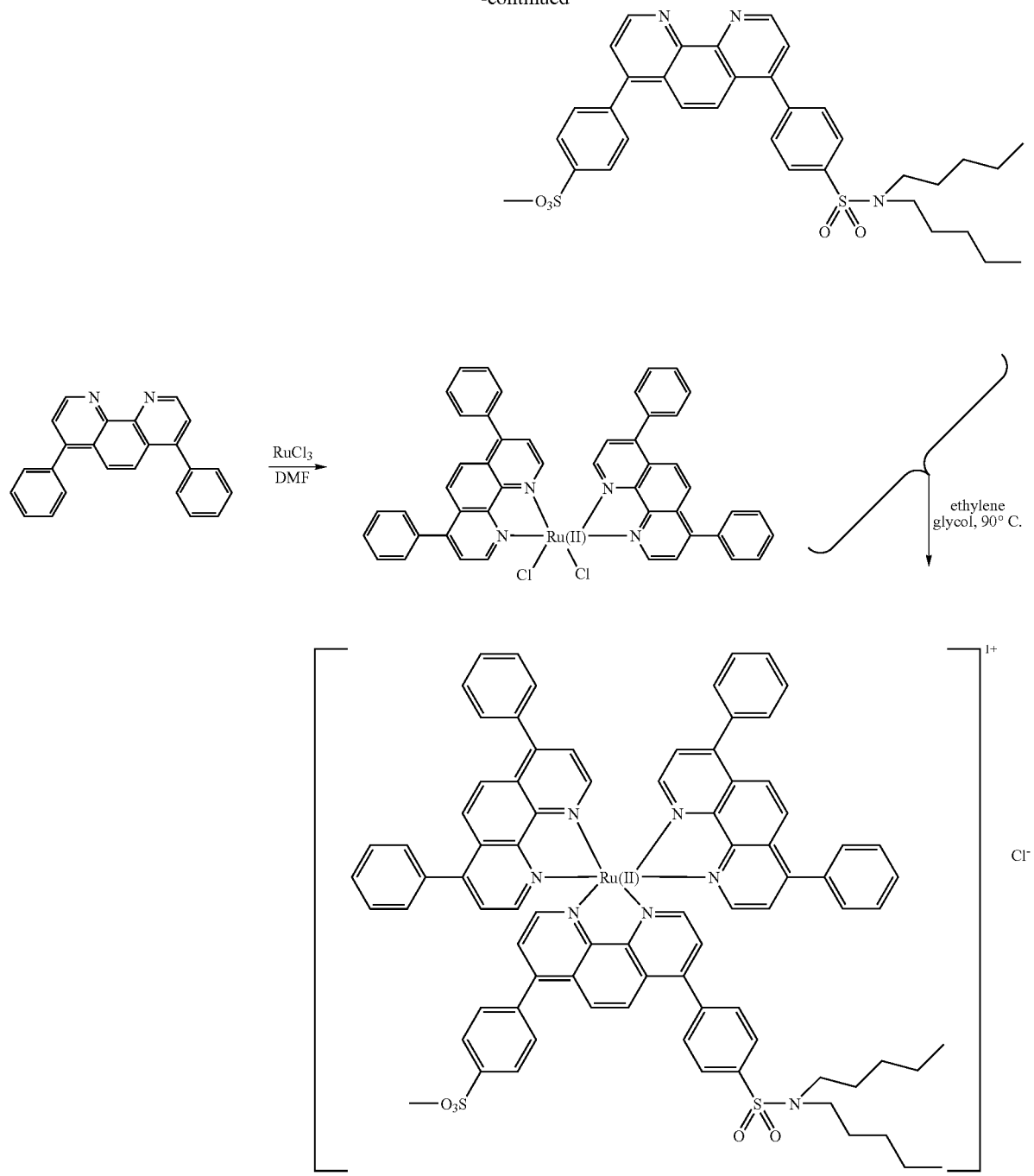

Synthesis of a Luminescent Rhenium Complex

A luminescent rhenium complex may be prepared as now described, merely by way of example. For example, a luminescent rhenium complex may be prepared by substituting at least one suitable ligand for at least one ligand of Re(CO)$_5$Cl, in any suitable manner, such as that shown in Scheme 3 below. The preparation may be via any suitable method, such as any previously known method, for example. (See Guo et al., *Anal. Biochem.*, 254, 179-186 (1997); Li et al, *Chem. Phys. Lipids*, 99, 1-9 (1999); and Smithback et al, *Inorg. Chem.*, 45, 2163-2174 (2006), for example.)

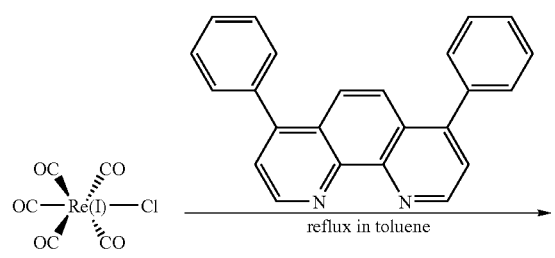

Scheme 3

-continued

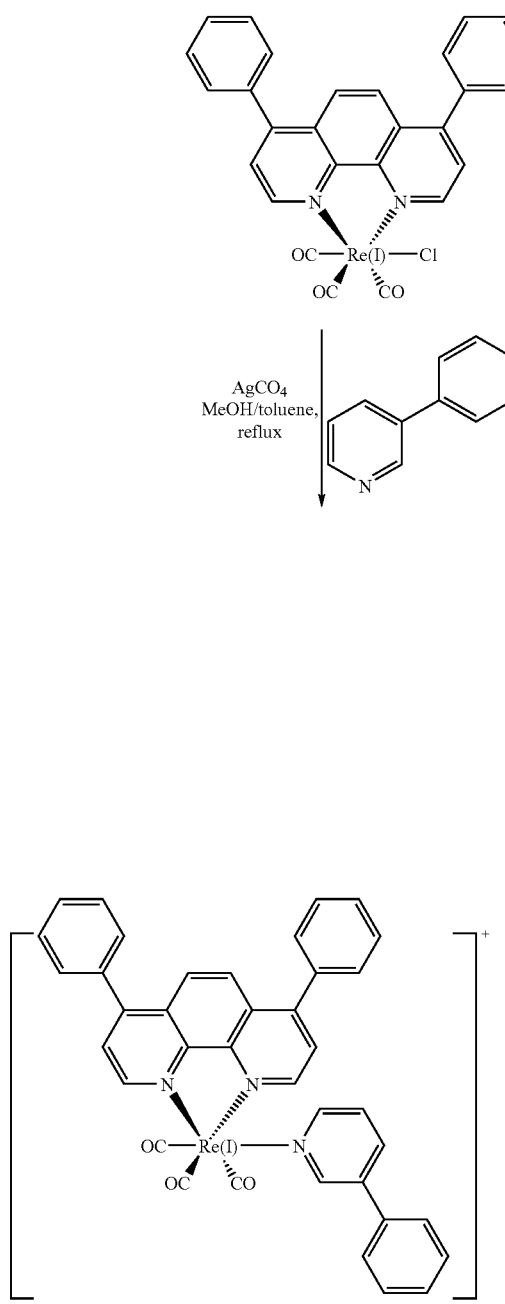

Synthesis of a Luminescent Rare Earth Metal Complex

A luminescent rare earth transition metal complex, such as a luminescent europium complex, for example, may be prepared as now described, merely by way of example. For example, a luminescent europium complex may be prepared by attaching a lipophilic substituent to a europium complex that comprises a reactive group, such as such a commercially available europium complex, for example, as shown in Scheme 4 below.

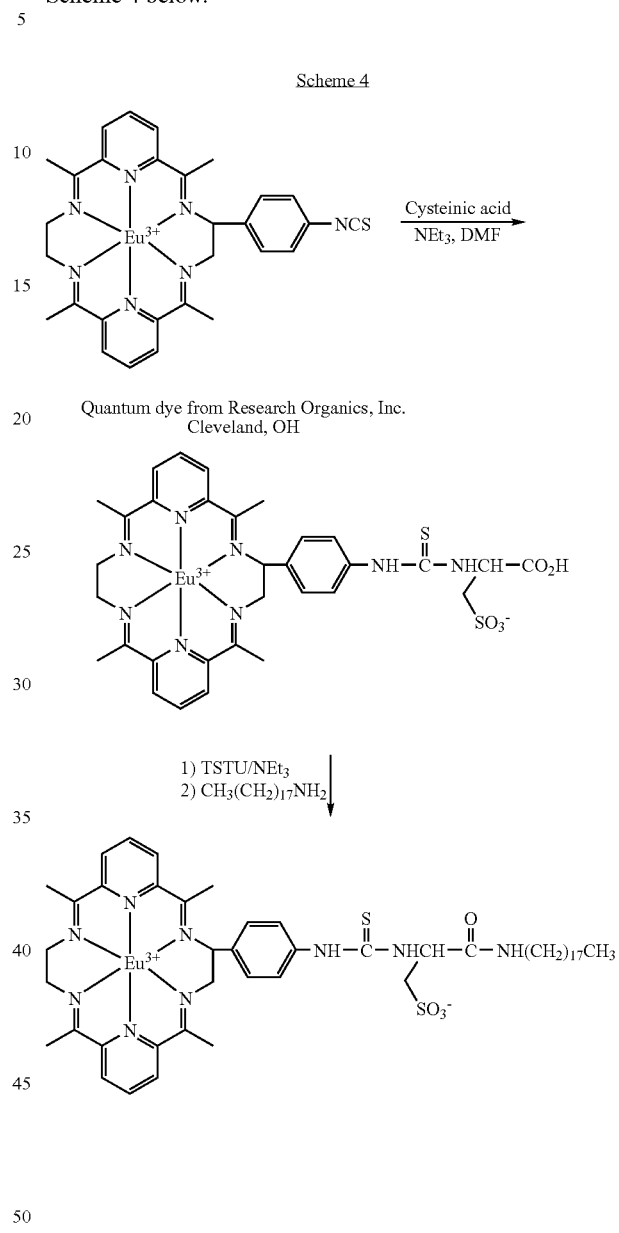

Further by way of example, a luminescent rare earth transition metal complex may be prepared by preparing a suitable ligand or suitable ligands, at least one of which comprises a relatively lipophilic substituent, and complexing the ligand(s) so prepared with a suitable rare earth transition metal. Any suitable method of preparing a ligand capable of chelating a rare earth transition metal, such as any previously known method, for example, may be employed, and may be suitably modified for preparing a ligand comprising a relatively lipophilic substituent.

Luminescent Metal Complexes

Various luminescent metal complexes or compositions are shown in Table 1 below.

TABLE 1

Luminescent Metal Complexes

| Complex No. | Representative Structure |
| --- | --- |
| 1 | |
| 2 | |
| 3 | Li et al., Chem. Phys. Lipids, 99, 1-9 (1999). |
| 4 | |

TABLE 1-continued
Luminescent Metal Complexes
| Complex No. | Representative Structure |
| --- | --- |
| 5 | 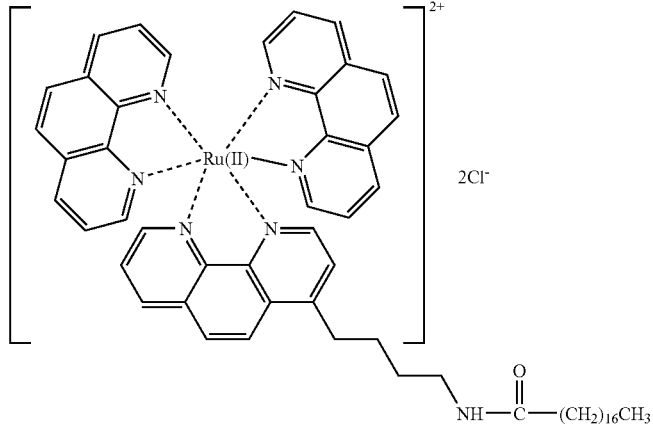 |
| 6 | 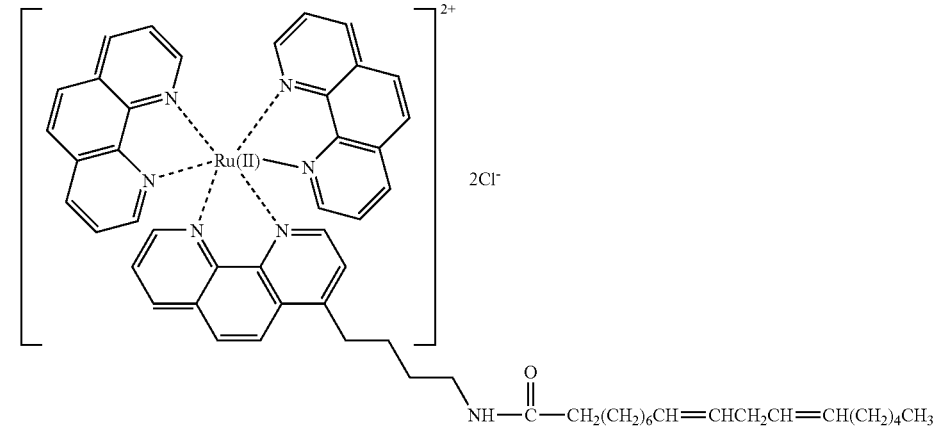 |
| 7 | 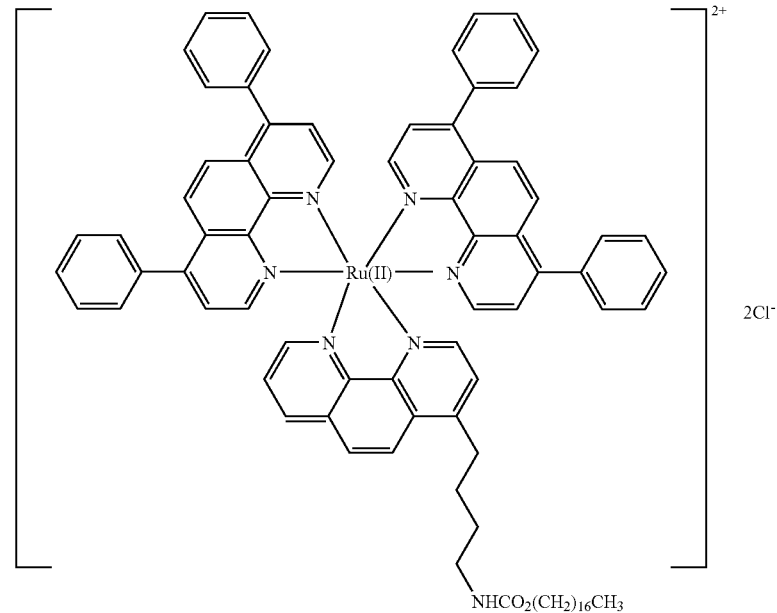 |

TABLE 1-continued
Luminescent Metal Complexes
| Complex No. | Representative Structure |
|---|---|
| 8 | 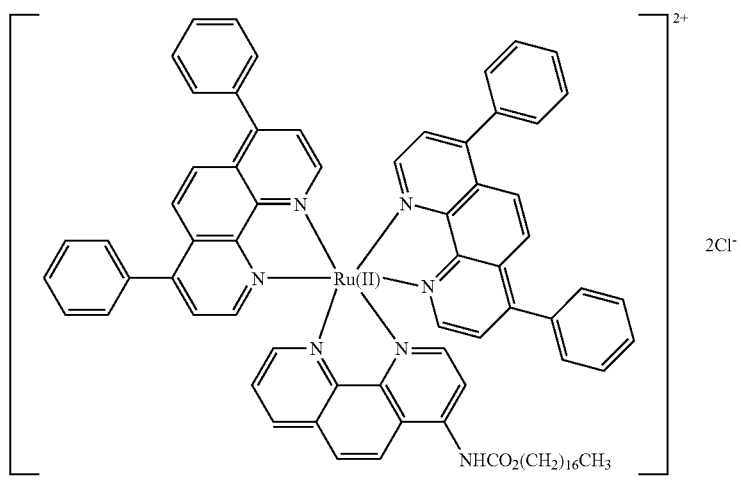 |
| 9 | 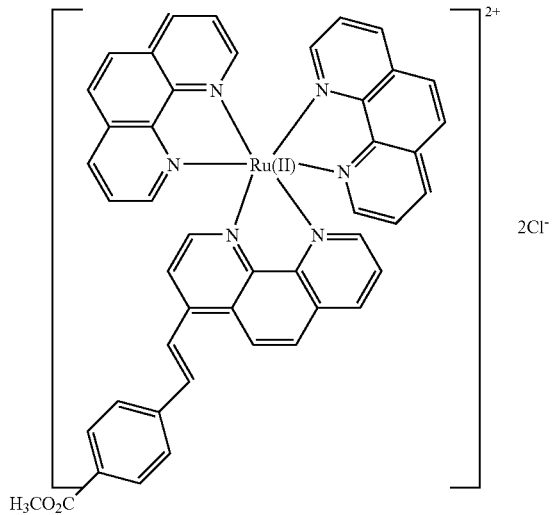 |

TABLE 1-continued
Luminescent Metal Complexes
| Complex No. | Representative Structure |
| --- | --- |
| 10 | 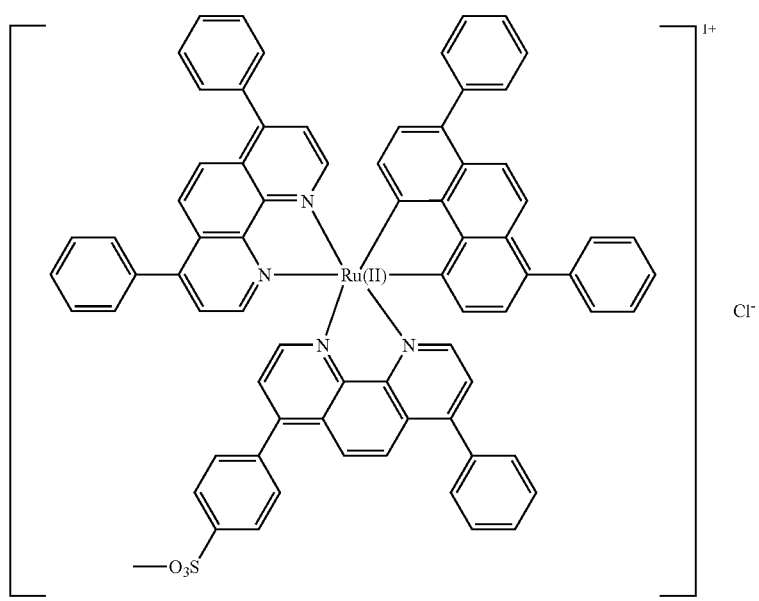 |
| 11 | 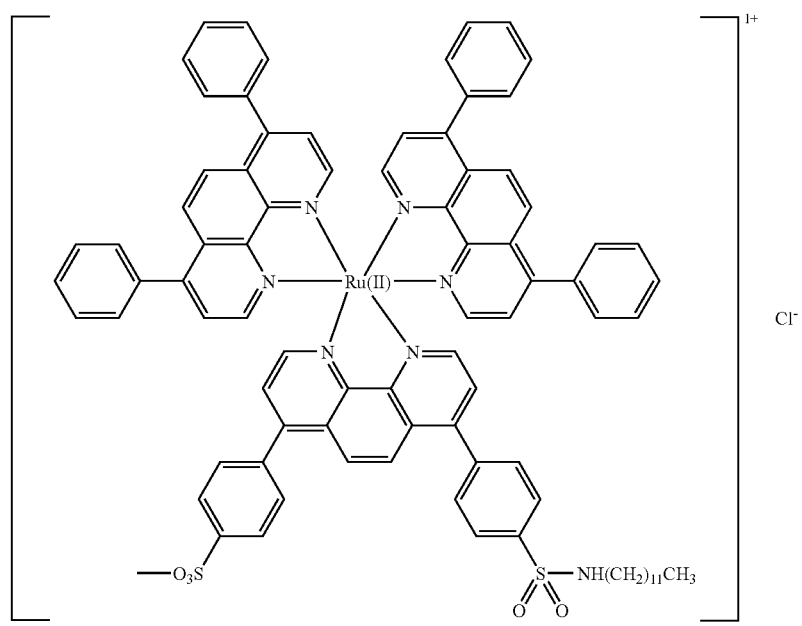 |

TABLE 1-continued
Luminescent Metal Complexes
| Complex No. | Representative Structure |
|---|---|
| 12 | 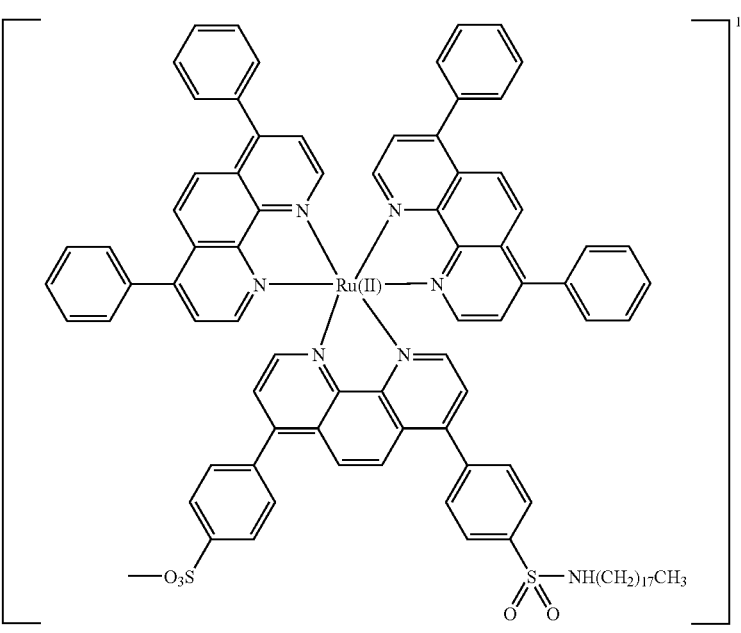 |
| 13 | 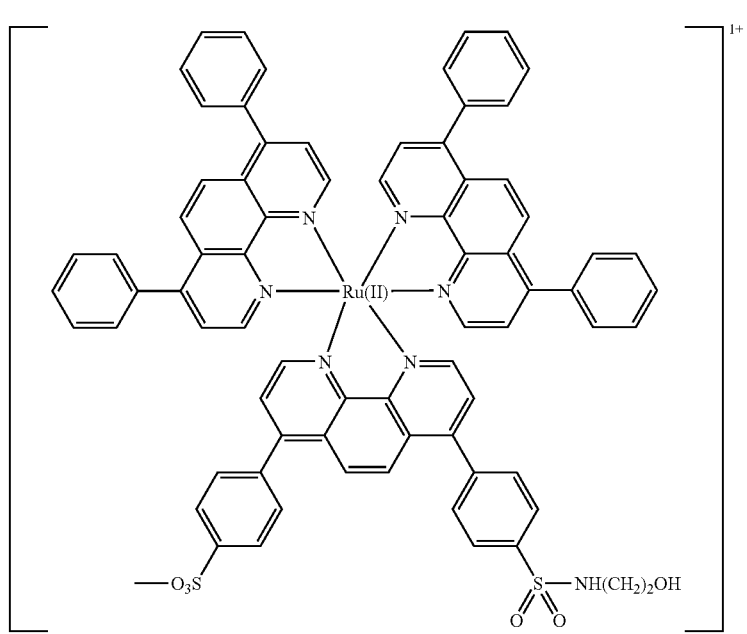 |

TABLE 1-continued
Luminescent Metal Complexes
| Complex No. | Representative Structure |
|---|---|
| 14 | 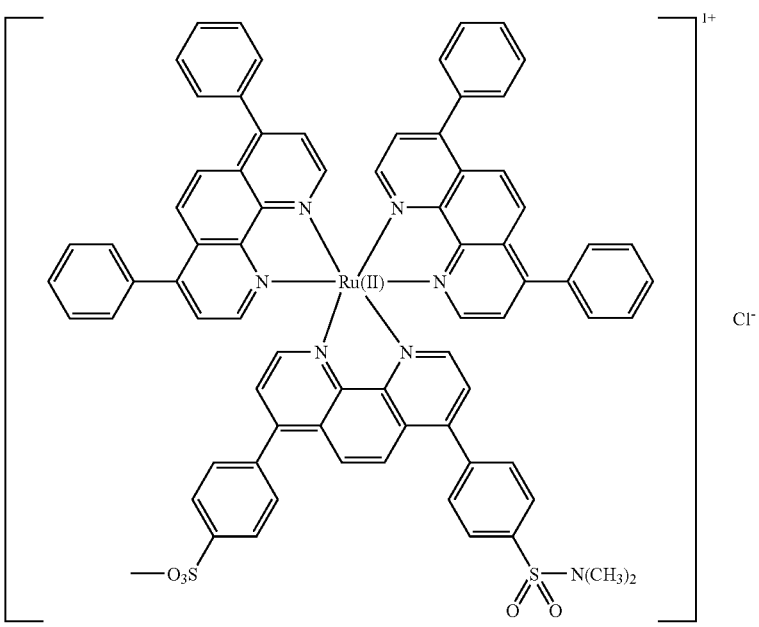 |
| 15 | 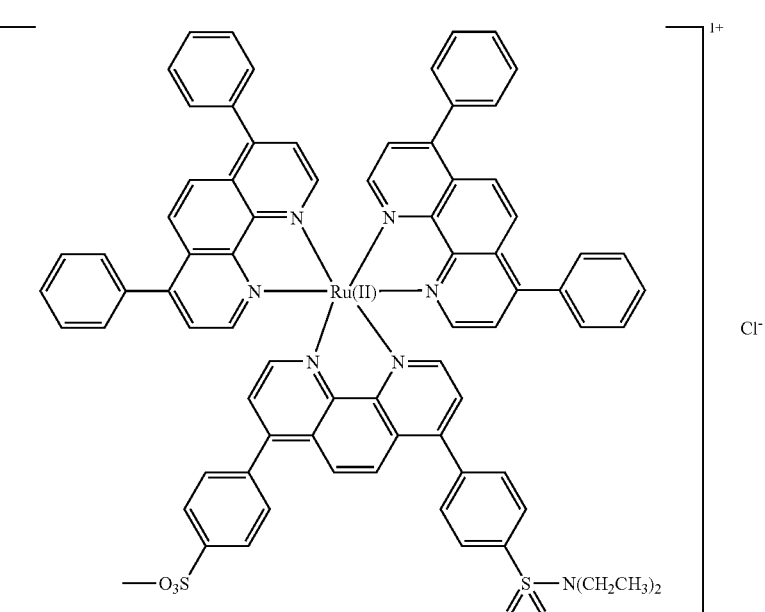 |

TABLE 1-continued
Luminescent Metal Complexes
| Complex No. | Representative Structure |
|---|---|
| 16 | 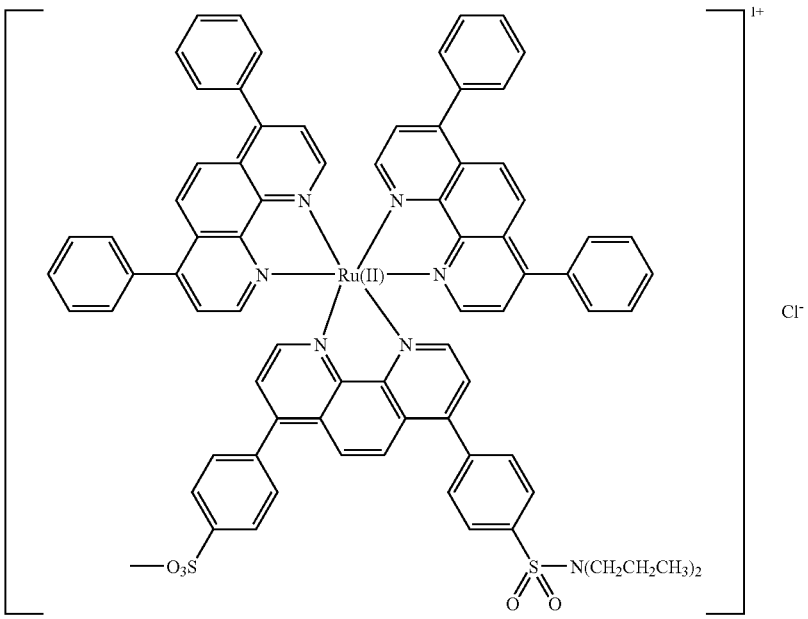 |
| 17 | 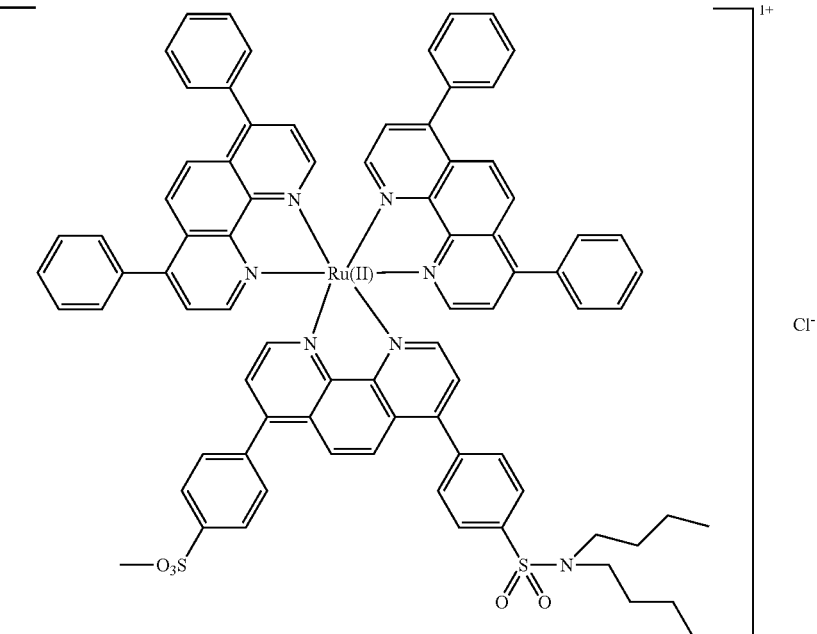 |

TABLE 1-continued
Luminescent Metal Complexes
| Complex No. | Representative Structure |
|---|---|
| 18 | 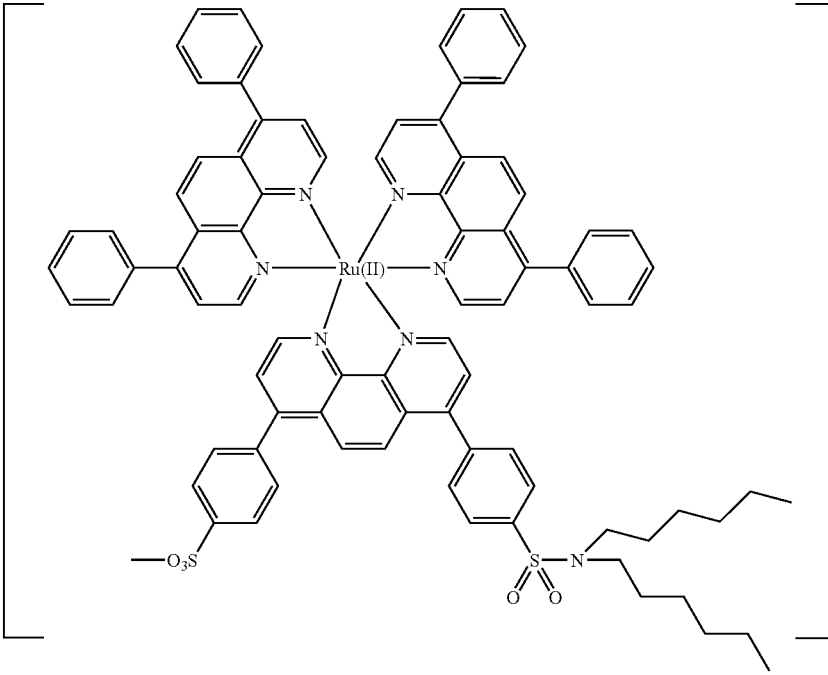 |
| 19 | 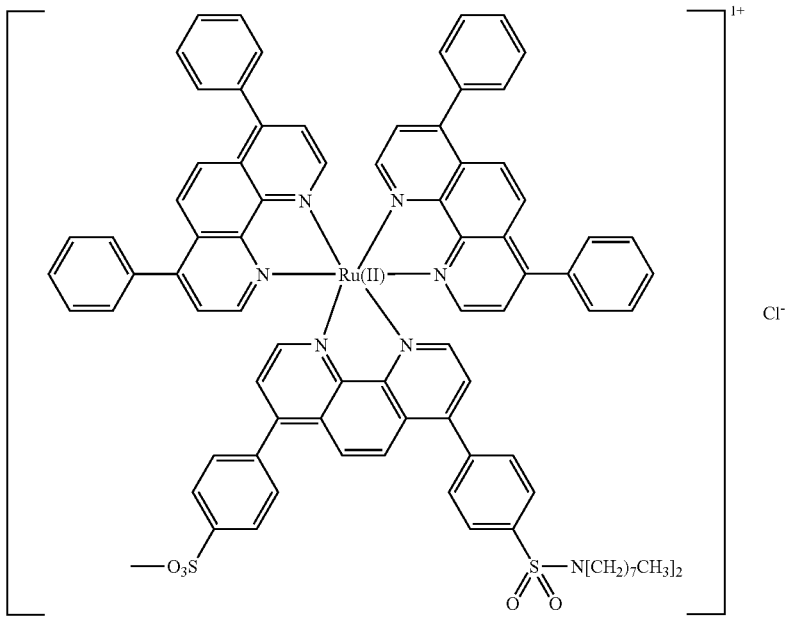 |

TABLE 1-continued
Luminescent Metal Complexes
| Complex No. | Representative Structure |
|---|---|
| 20 | 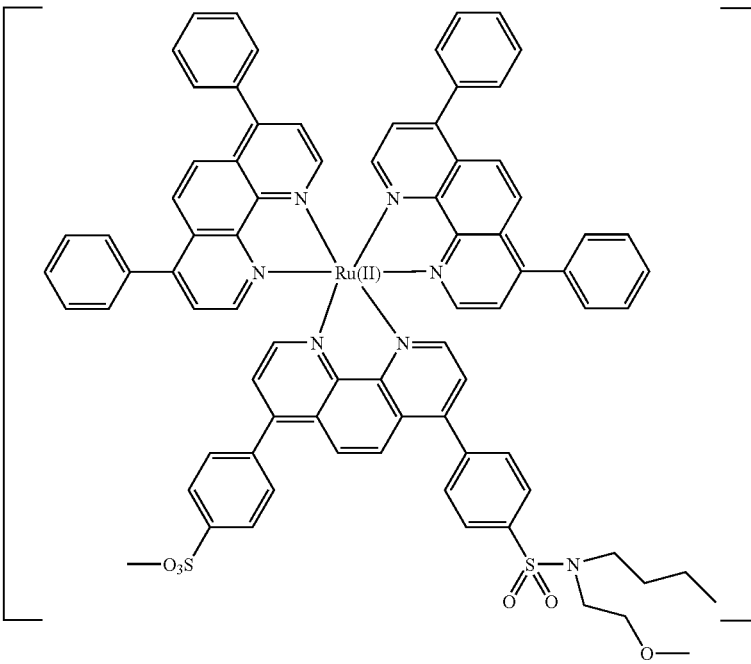 |
| 21 | 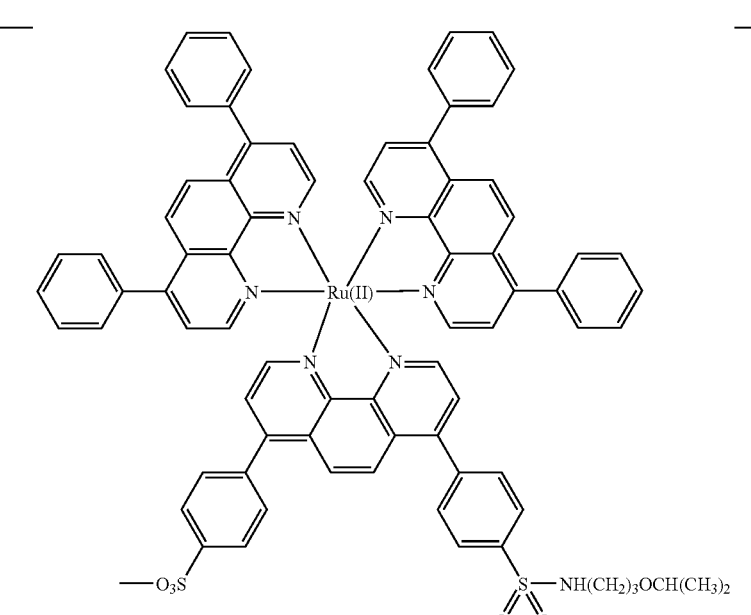 |

TABLE 1-continued
Luminescent Metal Complexes
| Complex No. | Representative Structure |
|---|---|
| 22 | 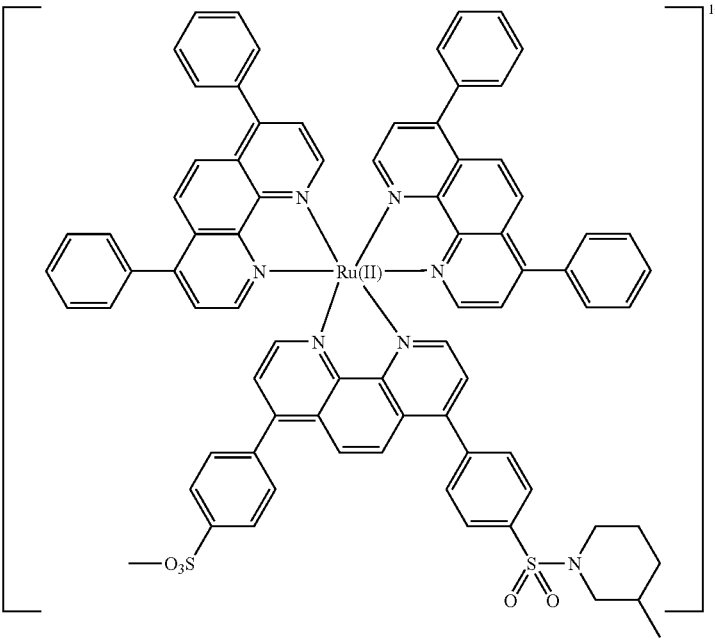 |
| 23 | 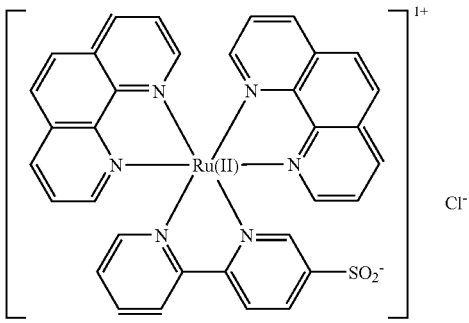 |
| 24 | 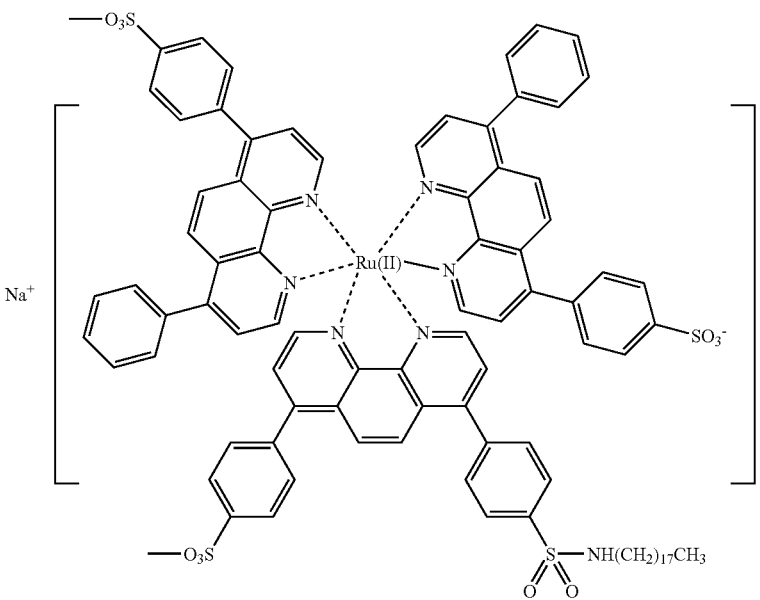 |

TABLE 1-continued

Luminescent Metal Complexes

| Complex No. | Representative Structure |
| --- | --- |
| 25 | 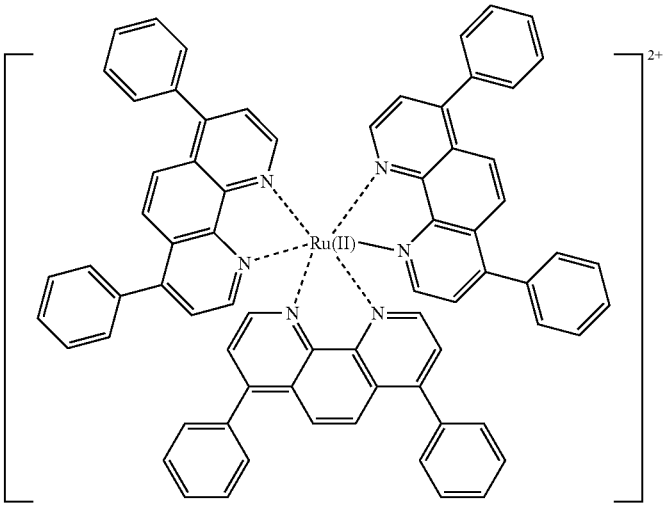 |

At least one of the luminescent rhenium complexes shown in Table 1, namely, Complex No. 3 of Table 1, was previously known, although not in connection with at least one application, namely, staining poly(amino acids).

A luminescent metal complex, such as any described herein, may be useful for staining and/or detecting poly (amino acids) in any of a variety of environments. For example, such a complex may be useful for staining poly (amino acids) that are immobilized relative to a gel matrix or a surface. The term "poly(amino acids)" encompasses proteins, peptides, and polypeptides, for example, such as any of same that comprise at least one natural and/or unnatural amino acid. Poly(amino acids) may comprise at least one natural and/or unnatural modifying chemical group, such as a carbohydrate, a phosphate, a lipid, a nucleic acid, and/or the like, merely by way of example. In general, proteins may be distinguished from one another on the basis of any associated modifying group or groups. By way of example, a protein comprising a carbohydrate may be referred to as a glycoprotein, a protein comprising a phosphate may be referred to as a phosphoprotein, and so on. Proteins associated with different modifying groups generally have different or distinct biological functions. In general, a luminescent metal complex described herein may stain proteins of different types in a relatively indiscriminative manner. Such a luminescent metal complex may be referred to as a luminescent total protein stain.

Poly(amino acids) may be present in any of a variety of samples, such as biological samples, for example. A biological sample may comprise a biological fluid, such as blood, urine, saliva, lymph fluid, cerebrospinal fluid, cell lysate, and/or the like, merely by way of example, a cell culture, a tissue sample, and/or a virus particle, merely by way of example. Poly(amino acids) of a sample may be stained directly by exposing the sample and a luminescent metal complex to one another, such as via incubation of the sample in the presence of the complex, for example. The exposure may be for a time sufficient for the luminescent metal complex to associate with poly(amino acids) of the sample, such as in any way described herein, for example.

Poly(amino acids), such as those present in a sample, for example, may be enriched and/or separated from one another, such as on the any of various properties, such as size or another physical property, or a biological property, merely by way of example. Merely by way of example, a suitable method of such enrichment and/or separation may comprise gel electrophoresis, density gradient, immobilization onto a surface, such as a membrane or a resin, for example. Poly (amino acids) may be stained with a luminescent metal complex, such as any described herein, before, at least partially during, at the end of, or after such enrichment and/or separation. Merely by way of example, poly(amino acids) immobilized relative to a gel matrix, such as an agarose gel matrix or a polyacrylamide gel matrix, for example, may be stained by exposing such poly(amino acids) to a luminescent metal complex, such as any described herein.

Poly(amino acids) immobilized relative to a gel or gel matrix may be stained using a luminescent metal complex, such as any described herein. Any of several staining methods may be used. For example, in a method that may be referred to as a pre-staining method, a sample solution comprising poly(amino acids) may be exposed to, such as mixed with, for example, a luminescent metal complex, such as any described herein, at a suitable concentration, such as any described herein, for example. The poly(amino acids) may be subjected to denaturing, such as via exposure to a denaturing agent or detergent, exposure to heat, and/or both, for example. In such a case, the sample solution may be exposed to, such as mixed with, for example, a denaturing agent or detergent, such as SDS, for example, at a suitable concentration, and/or exposed to heat.

Generally, in a pre-staining method, the working or staining concentration of the luminescent metal complex may be within the range from about 0.05 μM to about 10 μM, inclusive, relative to a working or staining solution. Generally, in a pre-staining method that comprises exposure to a denaturing agent or detergent, the working concentration of the denaturing detergent may be from about 0.02% to about 0.2% by volume, inclusive, such as about 0.1% by volume, for example, relative to a working or staining solution.

In a pre-staining method, once the sample is exposed to a luminescent metal complex, and optionally, a denaturing agent or detergent, as described above, the resulting solution or mixture may be incubated for a time sufficient for association of the luminescent metal complex and poly(amino acids) of the sample, such as for about 5 minutes to about 30 minutes, inclusive, merely by way of example. The incubation may be at any suitable temperature, such as around room temperature, merely by way of example. The resulting solution or mixture may be loaded onto a gel. The loaded gel may be subjected to an electrophoretic process, such as any suitable known electrophoretic process, for example. (See Roskams et al. (Editors), *Lab Ref: A Handbook of Recipes, Reagents, and Other Reference Tools for Use at the Bench*, Cold Spring Harbor Laboratory Press, Cold Spring Harbor, N.Y., 2002, including pages 72-80, for example). Following the electrophoretic process, separated poly(amino acids) associated with the gel may be visualized directly, or may be visualized following destaining and/or washing the gel sufficiently to reduce or to remove any undesirable background. Destaining and/or washing may comprising exposing the gel to a suitable dye-free agent, such as water, for example, or a suitable dye-free solution, such as an aqueous solution comprising at least one organic solvent, for example. A suitable organic solvent may be methanol, such as methanol in an amount of about 5% to about 10% by volume, inclusive, relative to the aqueous solution, for example, or may be acetic acid, such as acetic acid in an amount of about 2% to about 15% by volume, inclusive, relative to the aqueous solution, for example.

Further by way of example, in a method that may be referred to as an in-process pre-staining method, an undenatured sample or a denature sample may be associated with an electrophoretic medium, such as a gel or a gel matrix, for example, and a luminescent metal complex, such as any described herein, may be combined with or added to an electrophoretic buffer, such as a cathodic buffer, for example, that is used in an electrophoretic process. A sample comprising poly(amino acids) may be subjected to the electrophoretic process, such that the poly(amino acids) migrate, whereupon the luminescent metal complex may stain the migrating poly (amino acids). Following the electrophoretic process, separated poly(amino acids) associated with the medium may be visualized directly, or may be visualized following destaining and/or washing the medium sufficiently to reduce or to remove any undesirable background, as described above in connection with the pre-staining method. Merely by way of example, a suitable in-process pre-staining method may be similar to a pre-staining method that may be used in connection with any of the Lucy protein stains commercially available from Sigma-Aldrich Corporation of St. Louis, Mo.

Still further by way of example, in a method that may be referred to as a post-staining method, poly(amino acids) in a sample solution may be separated via an electrophoretic process, such as any described herein or any suitable known electrophoretic process, for example. Merely by way of example, such separation may be via SDS-PAGE. A gel comprising the separated poly(amino acids) may undergo staining. Optionally, a gel comprising the separated poly(amino acids) may be fixed via any suitable method or means, such as via such as any described herein or any suitable known fixing method or means, for example, before staining. Merely by way of example, the gel may be exposed to a suitable fixation solution. Poly(amino acids) associated with the gel, fixed or otherwise, may be exposed to a solution comprising a luminescent metal complex, such as any described herein, in a manner sufficient to stain poly(amino acids). The exposure may comprise incubation, such as that described in connection with the pre-staining method, for example. A post-staining method, such as that just described, for example, may be used in connection with a one-dimensional (1-D) gel, such as a 1-D PAGE gel, or a two-dimensional (2-D) gel, such as a 2-D PAGE gel, merely by way of example.

Poly(amino acids), such as those associated with a sample or a sample solution, may be associated with or immobilized on a membrane, such as a membrane associated with a process comprising manipulation of poly(amino acids), for example. An example of such a process is a western blot process. Poly(amino acids) that are associated with a membrane may be exposed to a luminescent metal complex, such as any described herein, in a manner sufficient to stain poly (amino acids). Merely by way of example, such poly(amino acids) may be exposed to such a luminescent metal complex in any suitable manner, such as any described herein, for example. Such exposure may comprise incubation of a poly (amino acids)-associated membrane in a solution comprising a luminescent metal complex, such as via any suitable incubation process described herein.

In staining applications, a luminescent metal complex may be used in solution, as described herein. A useful staining solution may be any suitable solution comprising at least one metal complex, such as any described herein. Optionally, such a staining solution may comprise at least one component selected from a water-miscible organic solvent, an acid, a buffering agent, an inorganic salt, a metal chelating agent, a detergent, a reducing agent, and/or any other agent that may facilitate staining and/or may facilitate reduction of background.

Poly(amino acids) may be immobilized relative to a gel or a membrane, as described herein. The poly(amino acids)-associated gel or membrane may be bathed in a staining solution, such as any described herein, in a manner sufficient for staining poly(amino acids). By way of example, a bath comprising poly(amino acids)-associated gel or membrane and the staining solution may be agitated, such as via a shaker or an orbital shaker, for example. Further by way of example, bathing or staining may be sustained for any suitable amount of time, such as from about 5 minutes to about overnight, inclusive, or anywhere therebetween, such as from about 15 minutes to about 3 hours, inclusive, for example. Generally, staining of poly(amino acids) using a luminescent metal complex described herein may take a few hours or less. Generally, staining of poly(amino acids) using a luminescent metal complex described herein for a longer time, such as overnight or longer, for example, does not result in undesirable over-staining. Generally, when a staining solution comprises a sufficient amount of an alcoholic solvent, such as methanol at a concentration of at least about 15% by volume, relative to the solution, for example, and a sufficient amount of an acid, such as acetic acid at a concentration of at least about 5% acetic acid, relative to the solution, for example, immobilized poly (amino acids) may be stained after an electrophoretic process without being fixed beforehand.

Generally, staining of poly(amino acids) using a luminescent metal complex described herein may produce relatively low background. As such, generally, stained poly(amino acids) may be visualized after an electrophoretic process without being destained or washed beforehand. Destaining or washing may be employed if suitable or desired, however, such as if better, greater, optimal, or maximal signal-to-noise ratio is sought, for example. Destaining or washing may be carried out by incubating and/or rinsing with a destaining or washing agent or solution in any suitable manner, such as any described herein. Merely by way of example, an aqueous solution optionally comprising methanol at a concentration of up to about 40% by volume, inclusive, relative to the solution, and/or acetic acid at a concentration of up to about 15% by volume, inclusive, relative to the solution, may be used for destaining or washing. Further, merely by way of example, a water-based solution comprising methanol at a concentration of from about 10% to about 30% by volume, inclusive, relative to the solution and acetic acid at a concentration of from about 5% to about 15% by volume, inclusive, relative to the solution may be used for rinsing, and subsequently, water may be used for washing for a suitable amount of time, such as from about 5 minutes to about 10 minutes, inclusive, for example. When a staining application produces a relative weak luminescent band, destaining or washing may be used to facilitate a determination as to whether or not the relatively weak luminescent band is a real luminescent band, as opposed to noise or background, for example. Destaining or washing may have drawbacks, however. By way of example, destaining or washing may weaken or wash away a real luminescent band, as opposed to just background noise. Further by way of example, destaining or washing may lengthen and/or complicate processing.

Following staining, and optionally destaining or washing, poly(amino acids) or a medium associated with same may be illuminated with light of suitable wavelength to produce luminescence or a luminescent signal. Any suitable illumination method or means, may be employed. Merely by way of example, a UV transilluminator, a laser-based gel scanner, a Dark Reader from Clare Chemical Research, Inc. (Dolores, Colo.), and/or the like, may be employed.

In general, a suitable illuminating instrument may be chosen based on the excitation spectrum of a luminescent metal complex that was employed in staining the poly(amino acids). For example, in general, a luminescent metal complex described herein may be excited by ultraviolet (UV) light, such as light having a wavelength in a range of from about 200 nm to about 370 nm, inclusive. As such, in general, a UV transilluminator may be used to illuminate poly(amino acids) or a medium associated with same that has been stained using a luminescent metal complex described herein.

A luminescent metal complex described herein may be excited by UV light, as just described, and/or by visible light, such as light having a wavelength in a range from about 400 nm to about 550 nm, inclusive. As such, a UV transilluminator and/or an excitation instrument that employs a visible light excitation source may be used to illuminate poly(amino acids) or a medium associated with same that has been stained using such a luminescent metal complex. Merely by way of example, a luminescent ruthenium complex described herein may be excited by light associated with the UV spectral region, such as that comprising wavelengths near about 300 nm, for example, and light associated with the visible spectral region, such as that comprising wavelengths in a range of from about 400 nm to about 500 nm, inclusive, for example. An example of such a luminescent ruthenium complex is Complex No. 4 of Table 1, the excitation and emission spectra of which are shown in FIG. 5. Such a luminescent metal complex may be compatible with UV transilluminator that employs excitation light having a wavelength of about 300 nm, for example, a Dark Reader from Clare Chemical Research, Inc. (Dolores, Colo.), and/or a laser-based scanner that employs a laser source, such as an argon laser source, of excitation light having a wavelength of about 488 nm, for example. Luminescence or a luminescent signal may be detected in any appropriate manner, such as via visual inspection, photography, such as camera or film photography, and/or the like, merely by way of example.

It is contemplated that any suitable staining and/or detection scheme, method, means, or variation thereof, may be employed. Merely by way of example, a sample comprising poly(amino acids) may be associated with a sieving medium, such as a sieve or a sieving matrix, for example, a density gradient, such as a sedimentation density gradient or a buoyant density, for example, an inert medium or matrix, such as a filtering membrane, a testing strip, a solid support, a semi-solid support, for example, and/or the like. It is contemplated that a sample comprising poly(amino acids) so associated may be processed and stained in any suitable manner, such as any described herein or any suitable modification thereof, and may be subjected to detection in any suitable manner, such as any described herein or any suitable modification thereof.

EXAMPLES

The Examples set forth below include various preparations, in which all percentages are by volume, and various experiments.

Example 1

Preparation of Re[(CO)$_3$(bathocuproin)(4-phenylpyridine)]$^+$Cl$^-$, Complex No. 1 of Table 1

A mixture of Re[(bathocuproin)(CO)$_3$Cl] (50 mg) (prepared according to Guo et al., Anal. Biochem., 254, 179-186 (1997)), 4-phenylpyridine (1.5 equivalents) and silver perchlorate (1.5 equivalents) in dichlorobenzene (3 mL) was heated at 110° C. for 1 hour. The mixture was then cooled to room temperature, whereupon hexane was added and the precipitate was collected by suction filtration. The precipitate was purified by column chromatography to give a yellow solid, Re[(CO)$_3$(bathocuproin)(4-phenylpyridine)]$^+$Cl$^-$, Complex No. 1 of Table 1.

Example 2

Preparation of Re[(bathocuproin disulfonate)(CO)$_3$Cl]Na$_2$

A mixture of rhenium pentacarbonyl chloride (100 mg, 0.27 mmol) and bathocuproin sulfonate disodium salt (165 mg, 0.29 mmol) in ethylene glycol (3 mL) was heated at 100° C. overnight. As used in this Example and other Examples herein, overnight generally refers to a time of from about 8 hours to about 12 hours, although somewhat less or more time may be used. The mixture was then cooled to room temperature, whereupon it was triturated with EtOAc and the bright yellow precipitate was dried to a constant weight to give Re[(bathocuproin disulfonate)(CO)$_3$Cl]Na$_2$.

Example 3

Preparation of Re[(bathocuproin disulfonate)(CO)$_3$(4-phenylpyridine)]$^-$Na$^+$, Complex No. 2 of Table 1

Re[(bathocuproin disulfonate)(CO)$_3$(4-phenylpyridine)]$^-$Na$^+$, Complex No. 2 of Table 1, was prepared according to the procedure used in Example 1 to prepare Re[(bathocuproin)(CO)$_3$(4-phenylpyridine)]$^+$Cl$^-$, with the exception that Re[(bathocuproin disulfonate)(CO)$_3$Cl]Na$_2$, prepared according to Example 2, was used in place of Re[(bathocuproin)(CO)$_3$Cl].

Example 4

Preparation of Different Ru[(1,10-phenanthrolone)$_2$(4-(alkanoylaminobutyl)-1,10-phenanthroline)]$^{2+}$ 2Cl$^-$Complexes, Complex Nos. 4, 5 and 6 of Table 1

A general procedure, as described below, was used to prepare each of three ruthenium complexes, namely, each of Complex Nos. 4-6 of Table 1. Each of these complexes may be represented by the general structural formula set forth below as follows:

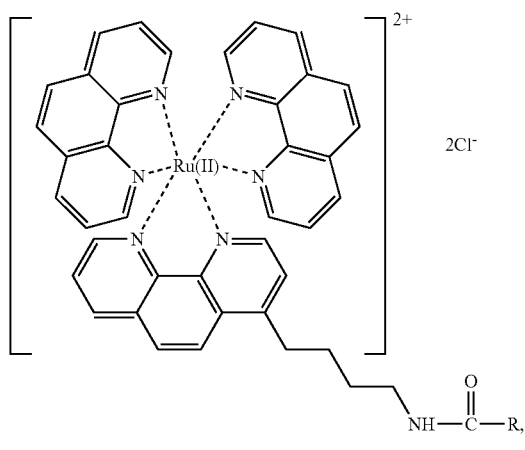

wherein R is different for each of the complexes, as may be represented by the different formulas set forth below as follows:

R=CH$_2$(CH$_2$)$_9$CH$_3$ for Complex No. 4 of Table 1;

R=CH$_2$(CH$_2$)$_{15}$CH$_3$ for Complex No. 5 of Table 1; or

R=CH$_2$(CH$_2$)$_6$CH=CHCH$_2$CH=CH(CH$_2$)$_4$—CH$_3$ for Complex No. 6 of Table 1.

The above-mentioned general procedure is now described. Et$_3$N (6 equivalents) and N,N,N',N'-tetramethyl-O—(N-succinimidyl)uranium tetrafluoroborate (TSTU) (0.95 equivalent) were added to a solution. For Complex Nos. 4, 5 and 6 of Table 1, respectively, the solution comprised CH$_3$(CH$_2$)$_{10}$CO$_2$H (0.07 mmol), CH$_3$(CH$_2$)$_{16}$CO$_2$H (0.07 mmol), and CH$_3$(CH$_2$)$_4$—CH=CHCH$_2$CH=CH(CH$_2$)$_7$CO$_2$H (0.07 mmol), respectively, in dimethylformamide (DMF) (1 mL) at room temperature. In each case, the resulting mixture was stirred at room temperature for 1 hour, whereupon aminolumitium 430 (0.48 equivalent) (Catalog No. 92002, Biotium Inc., Hayward, Calif.) was added. In each case, the resulting mixture was stirred at room temperature for 1 hour, whereupon the solvent was removed in vacuo and the residue was purified by column chromatography to give an orange solid, the product complex.

Example 5

Preparation of 4-(4-(octadecanoylamino)butyl)-1,10-phenanthroline

A mixture of octadecanoic acid (170 mg, 0.6 mmol) and thionyl chloride (4 mL) was heated at 60° C. for 1 hour. The mixture was then cooled to room temperature, whereupon it was concentrated in vacuo. Residue from this mixture was then dissolved in CH$_2$Cl$_2$ (10 mL), whereupon pyridine (5 equivalents) and 4-(aminobutyl)-1,10-phenanthroline (1 equivalent) (Wang et al., Adv. Funct. Mater., 12, 415-419 (2002)) were added. The resulting mixture was stirred at room temperature overnight and then poured into H$_2$O. The resulting precipitate was collected by suction filtration and dried to a constant weight to give 4-(4-(octadecanoylamino)butyl)-1,10-phenanthroline.

Example 6

Preparation of Ru[(bathophenanthroline)$_2$(4-(4-(octadecanoyamino)butyl)-1,10-phenanthroline)]$^{2+}$2Cl$^-$, Complex No. 7 of Table 1

A mixture of ruthenium(II) bis(bathophenanthroline) dichloride (50 mg, 0.06 mmol) and 4-(4-(octadecanoylamino)butyl)-1,10-phenanthroline (46 mg, 0.09 mmol), prepared according to Example 5, in DMF (2 mL) was heated at 90° C. overnight. The mixture was then cooled to room temperature, whereupon it was triturated with EtOAc. The resulting crude material was purified by column chromatography to give a red solid, Ru[(bathophenanthroline)$_2$(4-(4-(octadecanoyamino)butyl)-1,10-phenanthroline)]$^{2+}$2Cl$^-$, Complex No. 7 of Table 1.

Example 7

Preparation 5-(octadecanoylamino)-1,10-phenanthroline 5-(octadecanoylamino)-1,10-phenanthroline was prepared according to the procedure used in Example 5 to prepare 4-(4-(octadecanoylamino)butyl)-1,10-phenanthroline, with the exception that 1,10-phenanthrolin-5-amine was used in place of 4-(aminobutyl)-1,10-phenanthroline.

Example 8

Preparation of Ru[(bathophenanthroline)$_2$(5-(octadecanoylamino)-1,10-phenanthroline)]$^{2+}$2Cl$^-$, Complex No. 8 of Table 1

Ru[(bathophenanthroline)$_2$(5-octadecanoylamino)-1,1-phenanthroline)]$^{2+}$Cl$^-$, Complex No. 8 of Table 1, was prepared according to the procedure used in Example 6 to prepare Ru[(bathophenanthroline)$_2$(4-(4-(octadecanoyamino)butyl)-1,10-phenanthroline)]$^{2+}$2Cl$^-$, Complex No. 7 of Table 1, with the exception that 5-(octadecanoylamino)-1,10-phenanthroline, prepared according to Example 7, was used in place of 4-(4-(octadecanoylamino)butyl)-1,10-phenanthroline.

Example 9

Preparation of 4-(p-methoxycarbonylstyryl)-1,10-phenanthroline 4-methyl-1,10-phenanthroline (500 mg, 2.57 mmol) was added in one portion to a suspension of NaH (100 mg, 4.75 mmol) in anhydrous tetrahydrofuran (THF) (10 mL) at room temperature. The resulting mixture was stirred at room temperature overnight and then at 45° C. for 4 hours. The mixture was then cooled to room temperature, whereupon the precipitate was collected by suction filtration and dried to a constant weight in vacuo to give an off-white solid (800 mg), 4-(p-methoxycarbonylstyryl)-1,10-phenanthroline.

Example 10

Preparation of Ru[(1,10-phenanthroline)$_2$(4-(p-methoxycarbonylstyryl)-1,10-phenanthroline)]$^{2+}$2Cl$^-$, Complex No. 9 of Table 1

A mixture of ruthenium(II) bis(1,10-phenanthroline) dichloride (125 mg, 0.23 mmol) and 4-(p-methoxycarbonylstyryl)-1,10-phenanthroline (120 mg, 0.35 mmol), prepared according to Example 9, in DMF (3 mL) was heated at 90° C. overnight. The mixture was then cooled to room temperature, whereupon the mixture was triturated with EtOAc. The resulting crude material was purified by column chromatography to give an orange solid, Ru[(1,10-phenanthroline)$_2$(4-(p-methoxycarbonylstyryl)-1,10-phenanthroline)]$^{2+}$2Cl$^-$, Complex No. 9 of Table 1.

Example 11

Preparation of Bathophenanthroline Monosulfate

Bathophenanthroline (10 g) was added in small portion to a mechanically stirred solution of concentrated sulfuric acid (60 mL) cooled at 0-4° C., whereupon 30% fuming sulfuric acid (about 30 g) was added drop-wise. The resulting solution was then stirred at about 90° C. for about 2 hours, whereupon it was cooled to room temperature and then poured into cold ether. The resulting precipitate was collected and then separated on silica gel column using H$_2$O/CH$_3$CN (15%) to give bathophenanthroline monosulfate.

Example 12

Preparation of Ru[(bathophenanthroline)$_2$(bathophenanthroline mono-sulfate)]$^{1+}$Cl$^-$, Complex No. 10 of Table 1

Ru[(bathophenanthroline)$_2$(bathophenanthroline mono-sulfate)]$^{1+}$Cl$^-$, Complex No. 10 of Table 1, was prepared according to the procedure used in Example 6 to prepare Ru[(bathophenanthroline)$_2$(4-(4-(octadecanoyamino)butyl)-1,10-phenanthroline)]$^{2+}$2Cl$^-$, Complex No. 7 of Table 1, with the exception that bathophenanthroline was used in place of 4-(4-(octadecanoylamino)butyl)-1,10-phenanthroline.

Example 13

Preparation of Different 4-(4-(dialkylaminosulfo)phenyl)-7-(4-sulfophenyl)-1,10-phenanthroline Ligands and 4-(4-(monoalkylaminosulfo)phenyl)-7-(4-sulfophenyl)-1,10-phenanthroline Ligands A general procedure, as described below, was used to prepare each of various different monosulfonamide phenanthroline ligands. Each of these ligands may be represented by the general structural formula set forth below as follows:

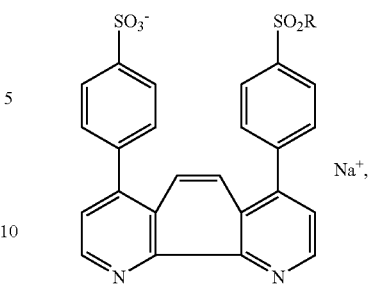

wherein R is different for each of the ligands, as represented by the different formulas set forth below as follows:

R=NH(CH$_2$)$_{11}$CH$_3$;

R=NH(CH$_2$)$_{17}$CH$_3$;

R=NH(CH$_2$CH$_2$OH);

R=N(CH$_3$)$_2$;

R=N(CH$_2$CH$_3$)$_2$;

R=N(CH$_2$CH$_2$CH$_3$)$_2$;

R=N(CH$_2$CH$_2$CH$_2$CH$_3$)$_2$;

R=N(CH$_2$CH$_2$CH$_2$CH$_2$CH$_2$CH$_3$)$_2$;

R=N(CH$_2$CH$_2$CH$_2$CH$_2$CH$_2$CH$_2$CH$_2$CH$_3$)$_2$;

R=N(CH$_2$CH$_2$OCH$_3$)$_2$;

R=NHCH$_2$CH$_2$CH$_2$OCH(CH$_3$)$_2$; or

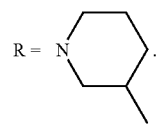

The above-mentioned general procedure is now described. A mixture of bathophenanthrolinedisulfonic acid disodium salt (0.37 mmol) and POCl$_3$ (2 mL) was heated at 90° C. for 3 hours. The mixture was then cooled to room temperature, whereupon Et$_2$O (50 mL) was added and the resulting suspension was stirred at room temperature for 1 hour. The Et$_2$O layer was decanted off and the solid residue was dried to constant weight in vacuo. The solid was then dissolved in DMF (3 mL) and the resulting solution was cooled at 0° C. In each case, triethylamine (3.7 mmol) and one of the amines (0.37 mmol) selected from the list of amines (R) above, were then added and the resulting mixture was stirred at room temperature for 1 hour. The DMF was removed in vacuo and the residue was suspended in saturated NaHCO$_3$ (20 mL) and stirred for 1 hour. The crude product was collected by suction filtration and dried to a constant weight to provide the various ligands, according to the amine selected.

Example 14

Preparation of Different Ru[(bathophenanthroline)$_2$(4-(4-(dialkylaminosulfo)phenyl)-7-(4-sulfophenyl)-1,10-phenanthroline)]$^{1+}$Cl$^-$ Complexes and Ru[(bathophenanthroline)$_2$(4-(4-(monoalkylaminosulfo)phenyl)-7-(4-sulfophenyl)-1,10-phenanthroline)]$^{1+}$Cl$^-$ Complexes, Complex Nos. 11-22 of Table 1

A general procedure, as described below, was used to prepare each of ten ruthenium complexes, namely, each of Complex Nos. 11-22 of Table 1. Each of these complexes may be represented by the general structural formula set forth below as follows:

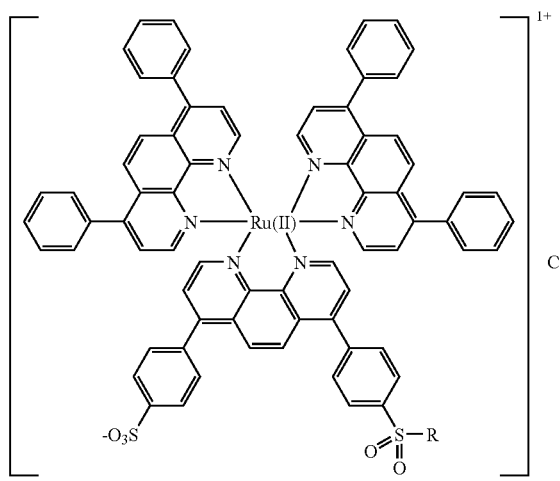

wherein R is different for each of the complexes, as may be represented by the different formulas set forth below as follows:

R=NH(CH$_2$)$_{11}$CH$_3$ for Complex No. 11 of Table 1;

R=NH(CH$_2$)$_{17}$CH$_3$ for Complex No. 12 of Table 1;

R=NH(CH$_2$CH$_2$OH) for Complex No. 13 of Table 1;

R=N(CH$_3$)$_2$ for Complex No. 14 of Table 1;

R=N(CH$_2$CH$_3$)$_2$ for Complex No. 15 of Table 1;

R=N(CH$_2$CH$_2$CH$_3$)$_2$ for Complex No. 16 of Table 1;

R=N(CH$_2$CH$_2$CH$_2$CH$_3$)$_2$ for Complex No. 17 of Table 1;

R=N(CH$_2$CH$_2$CH$_2$CH$_2$CH$_2$CH$_3$)$_2$ for Complex No. 18 of Table 1;

R=N(CH$_2$CH$_2$CH$_2$CH$_2$CH$_2$CH$_2$CH$_2$CH$_3$)$_2$ for Complex No. 19 of Table 1;

R=N(CH$_2$CH$_2$OCH$_3$)$_2$ for Complex No. 20 of Table 1;

R=NHCH$_2$CH$_2$CH$_2$OCH(CH$_3$)$_2$ for Complex No. 21 of Table 1; or

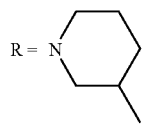

for Complex No. 22 of Table 1.

The above-mentioned general procedure is now described. A mixture of ruthenium(II) bis(bathophenanthroline) dichloride (60 mg, 0.072 mmol) (Collins et al., *Inorg. Chem.*, 38, 2020-2024 (1999)) and a bathophenanthroline monosulfonate monosulfonamide (1.2 equivalents), prepared according to Example 13, in DMF (1 mL), was heated at 90° C. overnight. A different bathophenanthroline monosulfonate monosulfonamide, as listed in order in Example 13, was used to prepare a different complex, as listed in corresponding order in this Example 14. The mixture was then cooled to room temperature, whereupon it as was triturated with EtOAc and the crude material was purified by column chromatography to give a red solid.

Example 15

Detection of Electrophoretically Separated Proteins in a SDS-PAGE Gel Using Complex No. 17 of Table 1 or SYPRO Ruby A gel preparation procedure is now described. Five μL of an unstained Precision Plus Protein Standard (Catalog No. 161-0363 from Bio-Rad Laboratories (Hercules, Calif.) (hereinafter, "Bio-Rad")) were separated on the left column of a polyacrylamide pre-cast gel (Catalog No. 161-1176, a Ready Gel from Bio-Rad) in running buffer containing 20 mM glycine, 2.5 mM Tris and 0.1% SDS, using a standard SDS-PAGE procedure. Five 5 μL of the same standard diluted five times were separated on the right column of the polyacrylamide pre-cast gel under the same conditions.

The foregoing procedure was used to prepare one gel, which was further processed as described below using a particular staining solution. Separately, the same procedure was used to prepare another gel, which was further processed as described below using a different staining solution.

One of the gels containing the separated proteins was stained by placing it in a staining solution comprising 2.5 μM of a monocationically net charged ruthenium complex, Complex No. 17 of Table 1, 30% MeOH, 14% acetic acid, and 0.2% Pluronic F-127, for 10 minutes, 30 minutes, 1 hour, and overnight. At the end of each of these periods, the gel was taken out of the solution, illuminated, and photographed, and if a further period remained, returned to the solution until the end of that further period. A UV transilluminator (300-nm wavelength) was used to illuminate the gel and Polaroid 667 black-and-white film was used to photograph the gel. The gel was not destained before being photographed.

The other of the gels containing the separated proteins was stained using SYPRO Ruby protein gel stain from Molecular Probes, Inc. (Eugene, Oreg.) in a manner similar to that just described in connection with Complex No. 17 of Table 1, with the following exceptions: the manufacturer's staining protocol, which required fixation prior to staining, was followed; staining times were 1 hour and overnight; and as to the overnight staining time, the gel was not destained before being photographed in one instance, and was destained before being photographed in another instance.

The photographs resulting from this Example 15 are shown in FIG. 1. The gel stained with SYPRO Ruby was observed at earlier intervals than those shown in the photographs, such as upon 10 minutes of staining, for example, but luminescent bands were not then discernible and thus could not be photographed. A comparison of the photographs associated with Complex No. 17 of Table 1 and those associated with the SYPRO Ruby stain demonstrates that the former stains proteins much more clearly or visibly in much less time, and is thus much more sensitive. A monocationically net charged metal complex, such as Complex No. 17 of Table 1, for example, may be capable of performing at least as well as, if not outperforming, SYPRO Ruby, in terms of stain speed, sensitivity, desirable background, and/or desirable processing. A monocationically net charged metal complex, such as Complex No. 4 of Table 1, for example, may be capable of providing good or acceptable results in terms of stain speed, sensitivity, desirable background, and/or desirable processing.

Example 16

Detection of Electrophoretically Separated Proteins in a SDS-PAGE Gel Using Complex No. 4 of Table 1

A gel was prepared according to the gel preparation procedure described in connection with Example 15. The gel was then processed as now described. The gel was placed in a fixation solution comprising 50% MeOH and 7% acetic acid for 30 minutes to fix the gel. The fixed gel was then stained by placing it in a staining solution comprising 1.2 µM of a dicationically net charged ruthenium complex, Complex No. 4 of Table 1, 1% ethanol and 0.45% of lactic acid in $H_2O$. The gel was illuminated and photographed after the gel had been stained for 4 hours, and after the gel had been stained overnight, in the manner described in connection with Example 15. The gel was not destained before being photographed.

The photographs resulting from this Example 16 are shown in FIG. 2. The photographs demonstrate that Complex No. 4 of Table 1 may stain proteins in gels with good speed, good sensitivity, and very low background. The photographs also demonstrate that Complex No. 4 of Table 1 provides acceptable results without a destaining process. A comparison of the photographs associated with Complex No. 4 of Table 1, as shown in FIG. 2, and those associated with the SYPRO Ruby stain, as shown in FIG. 1, demonstrates that the former stain is capable of performing at least as well as, if not outperforming, SYPRO Ruby, without destaining, in terms of stain speed, sensitivity, desirable background, and/or desirable processing. A dicationically net charged metal complex, such as Complex No. 4 of Table 1, for example, may be capable of providing good or acceptable results in terms of stain speed, desirable sensitivity, desirable background, and/or desirable processing.

Example 17

Detection of Electrophoretically Separated Proteins in a SDS-Page Gel Using Complex No. 2 of Table 1

A gel was prepared according to the gel preparation procedure described in connection with Example 15. The gel was then processed as now described. The gel was placed in a fixation solution comprising 50% MeOH and 7% acetic acid for 1 hour to fix the gel. The fixed gel was then stained by placing it in a staining solution comprising 2 µM of a monoanionically net charged rhenium complex, Complex No. 2 of Table 1, and 1% ethanol, in $H_2O$. The gel was illuminated and photographed after the gel had been stained overnight, in the manner described in connection with Example 15. The gel was not destained before being photographed.

The photographs resulting from this Example 17 are shown in FIG. 3. The photographs demonstrate that Complex No. 2 of Table 1 may stain proteins in gels with good sensitivity and relatively low background. The photographs also demonstrate that Complex No. 2 of Table 1 provides acceptable results without a destaining process. A comparison of the photographs associated with Complex No. 2 of Table 1, as shown in FIG. 3, and those associated with the SYPRO Ruby stain, as shown in FIG. 1, demonstrates that the former stain is capable of performing at least as well as, if not outperforming, SYPRO Ruby, without destaining, in terms of stain speed, sensitivity, desirable background, and/or desirable processing. A luminescent rhenium complex, such as Complex No. 4 of Table 1, for example, may be capable of providing good or acceptable results in terms of desirable sensitivity, desirable background, and/or desirable processing.

Example 18

Detection of Electrophoretically Separated Proteins in SDS-Page Gels Using $[Ru(Bpy)_3]Cl_2$, $[Ru(1,10\text{-phenanthroline})_3]Cl_2$, or Complex No. 22 of Table 1

Three gels were prepared, each according to the gel preparation procedure described in connection with Example 15. One of the gels was stained using a staining solution comprising 1.5 µM of $[Ru(bpy)_3]Cl_2$ (Aldrich, Milwaukee, Wis.), wherein "bpy" is unsubstituted 2,2'-bipyridine, 30% MeOH and 14% acetic acid. Another of the gels was stained using a staining solution comprising 1.5 µM of $[Ru(1,10\text{-phenanthroline})_3]Cl_2$ (Aldrich, Milwaukee, Wis.), 30% MeOH and 14% acetic acid. The remaining gel was stained using a staining solution comprising 1.5 µM of a monoanionically net charged ruthenium complex, Complex No. 22 of Table 1, 30% MeOH and 14% acetic acid. Each gel was stained by incubating it in the appropriate staining solution at room temperature for 90 minutes, whereupon each gel was taken out of the staining solution, illuminated and photographed in the manner described in connection with Example 15. No gel was destained before being photographed.

The photographs resulting from this Example 18 are shown in FIG. 4. The staining solutions used in this Example 18 comprised $[Ru(bpy)_3]Cl_2$, a ruthenium complex comprising three unsubstituted 2,2'-bipyridine (bpy) ligands; $[Ru(1,10\text{-phenanthroline})_3]Cl_2$, a ruthenium complex comprising three unsubstituted phenanthroline ligands; or Complex No. 22 of Table 1. The photographs demonstrate that the staining solution that comprised $[Ru(bpy)_3]Cl_2$ and the staining solution that comprised $[Ru(1,10\text{-phenanthroline})_3]Cl_2$ failed to stain proteins under the given conditions. The photographs also demonstrate that the staining solution that comprised Complex No. 22 of Table 1 succeeded in staining the proteins under the given conditions. Under conditions appropriate for protein staining, a positively net charged complex of insufficient lipophilicity, such as $[Ru(bpy)_3]Cl_2$ or $[Ru(1,10\text{-phenanthroline})_3]Cl_2$, for example, may be insufficient to stain proteins, while a positively charged ruthenium complex of sufficient lipophilicity or comprising at least one substituent of sufficient lipophilicity, such as Complex No. 22 of Table 1, for example, may be sufficient to stain the proteins.

A relatively lipophilic luminescent metal complex has been described herein. Such a luminescent metal complex may be useful for staining and/or detecting poly(amino acids), such as proteins, peptides, and/or polypeptides. Such poly(amino acids) may be associated with any of a variety of environments, such as live or dead cells, live or dead virus particles, and/or live or dead tissue samples, for example, may be associated with biological fluids, such as any described herein, for example, and/or may be associated with a medium, such as any described herein, for example. Merely by way of example, a luminescent metal complex may be useful for staining and/or detecting poly(amino acids), such as proteins, for example, that are immobilized in a gel or a gel matrix, such as a polyacrylamide gel associated with SDS-PAGE, or that are immobilized on a surface, such as a membrane associated with western blot. A luminescent metal complex described herein may be used for such staining and/or detection applications, and may be associated with various positive attributes, such as relatively low background luminescence, good luminescent signal strength, good sensitivity, relatively quick staining, and/or relatively simple procedures or protocols, merely by way of example.

Useful luminescent metal complexes have been described herein. Merely by way of example, a relatively lipophilic, luminescent ruthenium complex that is suitable for detecting the presence or absence of poly(amino acids), such as immobilized proteins in a gel matrix or on a solid surface, for example, has been described. Useful methods for protein gel staining have also been described herein. Merely by way of example, a method of using a relatively lipophilic metal complex, such as a relatively lipophilic, positively net charged ruthenium complex, for example, for staining poly(amino acids), such as post-gel staining of proteins, for example, has been described. Useful methods of preparing any of various luminescent metal complexes described herein and useful methods of using any of these complexes have also been described. Useful compositions, solutions, and kits comprising a luminescent metal complex described herein that are suitable for staining, detecting, and/or identifying poly(amino acids), such as immobilized proteins, for example, have also been described.

The references listed below, some of which may have been mentioned previously herein, are incorporated herein by reference.
Alford et al., J. Chem. Soc. Perkin. Trans. II, 705-709 (1985)
Collins et al., Inorg. Chem., 38, 2020-2024 (1999)
García-Fresnadillo et al., Helv. Chim. Acta, 84, 2708-2730 (2001)
Guo et al., Anal. Biochem., 254, 179-186 (1997)
Lamanda et al., Proteomics, 4, 599-608 (2004)
Li et al., Chem. Phys. Lipids, 99, 1-9 (1999)
Lim et al., Anal. Biochem., 245, 184-195 (1997)
Mackintosh et al., Proteomics, 3, 2273-2288 (2003)
Nishihara et al., Electrophoresis, 23, 2203-2215 (2002)
Rabilloud et al., Proteomics, 1, 699-704 (2001)
Roskams et al. (Editors), Lab Ref: A Handbook of Recipes, Reagents, and Other Reference Tools for Use at the Bench, Cold Spring Harbor Laboratory Press, Cold Spring Harbor, N.Y., 2002, including pages 72-80
Smithback et al., Inorg. Chem., 45, 2163-2174 (2006)
Steinberg et al., Anal. Biochem., 239, 223-237 (1996)
Steinberg et al., Electrophoresis, 21, 486-496 (2000)
Wang et al., Adv. Funct. Mater., 12, 415-419 (2002)
Paper print-out from www.gfschemical.com/chemicals/gf-schem-1597.asp, bearing Page 1 of 2, Page 2 of 2, and a date of Nov. 13, 2006
Bhalgat et al., U.S. Pat. No. 6,316,267
Patton et al., International Application Published Under the Patent Cooperation Treaty (PCT) bearing International Publication No. WO 97/20213

Various modifications, processes, as well as numerous structures that may be applicable herein will be apparent. Various aspects, features or embodiments may have been explained or described in relation to understandings, beliefs, theories, underlying assumptions, and/or working or prophetic examples, although it will be understood that any particular understanding, belief, theory, underlying assumption, and/or working or prophetic example is not limiting. Although the various aspects and features may have been described with respect to various embodiments and specific examples herein, it will be understood that any of same is not limiting with respect to the full scope of the appended claims or other claims that may be associated with this application.

What is claimed is:

1. A method of detecting the presence of poly(amino acids) in a sample, the method comprising:

a) mixing the sample with a solution comprising a luminescent complex to form stained poly(amino acids), wherein the stained poly(amino acids) consists of the poly(amino acids) and the luminescent complex and wherein the luminescent complex has a formula:

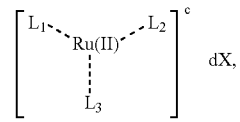

wherein $L_1$, $L_2$, and $L_3$ are each independently a ligand; wherein one or more of $L_1$, $L_2$, and $L_3$ comprises at least 20 carbon atoms, renders the luminescent complex sufficiently lipophilic and interacts with the total poly(amino acids) of the sample via direct hydrophobic and wherein at least two of $L_1$, $L_2$ and $L_3$ are independently selected from 2,2'-bipyridine, a substituted 2,2'-bipyridine of less than 23 carbon atoms, 1,10-phenanthroline, and a substituted 1,10-phenanthroline of less than 25 carbon atoms and wherein c is a charge of +1 or +2, X is a counterion, and d is the number of X; and b) detecting light emission from the stained poly(amino acids), thereby detecting the presence of the poly(amino acids).

2. The method of claim 1, wherein
at least two of the $L_1$, $L_2$ and $L_3$ are independently selected from 2,2'-bipyridine, 4,4'-dimethyl-2,2'-bipyridine, 3,4,3',4'-tetramethyl-2,2'-bipyridine, 4,4'-diphenyl-2,2'-bipyridine, 1,10-phenanthroline, 4-methyl-1,10-phenanthroline, 5-methyl-1,10-phenanthroline, 4,7-dimethyl-1,10-phenanthroline, 5,6-dimethyl-1,10-phenanthroline, 3,4,7,8-tetramethyl-1,10-phenanthroline, 5-phenyl-1,10-phenanthroline, bathophenanthroline, and 5-chloro-1,10-phenanthroline, any one of which is unsubstituted or substituted with one sulfonate group;
and the total number of sulfonate groups, if present in $L_1$, $L_2$ and $L_3$, combined is no more than 1.

3. The method of claim 1, wherein at least one of the $L_1$, $L_2$ and $L_3$ is 4,4'-dinonyl-2,2'-bipyridine or bathophenanthroline.

4. The method of claim 1, wherein at least one of the $L_1$, $L_2$ and $L_3$ is represented by the formula,

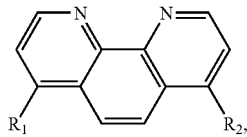

wherein:
$R_1$ is —H, phenyl, or sulfophenyl; and
$R_2$ is a C6 to C22 alkyl, the alkyl optionally comprising at least one hetero atom selected from halogen, nitrogen, oxygen, and sulfur; a phenyl, substituted with a C1 to C18 alkylaminosulfo substituent, wherein the alkyl thereof is linear or branched and optionally comprises an aryl and/or at least one oxygen atom; or a phenyl, unsubstituted or substituted with a C2 to C24 dialkylaminosulfo substituent, wherein the dialkyl thereof is linear or branched, optionally comprises an aryl and/or at least one oxygen atom, and optionally forms a saturated or unsaturated, substituted or unsubstituted, 4- to 7-membered ring, and the total number of sulfonate groups, if present in $L_1$, $L_2$ and $L_3$, is no more than 1.

5. The method of claim 4, wherein at least one ligand selected from ligand $L_1$ and ligand $L_2$ is 1,10-phenanthroline; c is 2+; $R_1$ is —H; and $R_2$ is represented by the formula, —$(CH_2)_4NHCOR_3$, wherein $R_3$ is a C7 to C17 alkyl.

6. The method of claim 4, wherein at least one ligand selected from ligand $L_1$ and ligand $L_2$ is bathophenanthroline; c is 1+; $R_1$ is sulfophenyl; and $R_2$ is represented by the formula, —$ArSO_2NR_4R_5$, wherein $R_4$ is —H or a C1 to C7 alkyl; $R_5$ is —H or a C1 to C7 alkyl; and optionally $R_4$ and $R_5$ in combination form a C4- to C7-membered ring, the ring optionally substituted once by a methyl or an ethyl, or twice by a methyl, twice by an ethyl, or twice, once by a methyl and once by a ethyl.

7. The method of claim 1, wherein at least one of the $L_1$, $L_2$ and $L_3$ is bathophenanthroline.

8. The method of claim 1, wherein the solution further comprises a detergent.

9. The method of claim 1, wherein the sample is associated with a gel or a surface.

10. The method of claim 9, wherein the gel comprises agarose, acrylamide, and/or polyacrylamide.

11. The method of claim 1, wherein the method further comprises electrophoretic processing of the sample.

12. The method of claim 11, wherein the step of (a) and the electrophoretic processing of the sample are at least partially concurrent.

13. The method of claim 11, wherein the step of (a) follows the electrophoretic processing of the sample.

14. The method of claim 11, wherein the step of (a) precedes the electrophoretic processing of the sample.

15. The method of claim 1, wherein the sample is associated with a membrane comprising nitrocellulose, nylon, and/or poly(vinylidene difluoride).

* * * * *